(12) United States Patent
Utsugi et al.

(10) Patent No.: US 8,175,686 B2
(45) Date of Patent: May 8, 2012

(54) EXTERNAL CONDITION CONTROL DEVICE BASED ON MEASUREMENT OF BRAIN FUNCTIONS

(75) Inventors: Kei Utsugi, Kawasaki (JP); Atsushi Maki, Fuchu (JP)

(73) Assignee: Hitachi, Ltd., Tokyo (JP)

( * ) Notice: Subject to any disclaimer, the term of this patent is extended or adjusted under 35 U.S.C. 154(b) by 901 days.

(21) Appl. No.: 12/039,864

(22) Filed: Feb. 29, 2008

(65) Prior Publication Data

US 2009/0036781 A1  Feb. 5, 2009

(30) Foreign Application Priority Data

Jul. 31, 2007  (JP) ................................ 2007-198249

(51) Int. Cl.
*A61B 6/00* (2006.01)
(52) U.S. Cl. .................. 600/473; 600/310; 600/544
(58) Field of Classification Search .................... 463/36; 600/310, 544, 545, 407, 437, 473; 607/45; 623/24; 250/221
See application file for complete search history.

(56) References Cited

U.S. PATENT DOCUMENTS

| | | | | |
|---|---|---|---|---|
| 4,926,969 A | * | 5/1990 | Wright et al. | 600/544 |
| 4,949,726 A | * | 8/1990 | Hartzell et al. | 600/544 |
| 5,571,057 A | * | 11/1996 | Ayers | 463/36 |
| 5,638,826 A | * | 6/1997 | Wolpaw et al. | 600/544 |
| 5,772,508 A | * | 6/1998 | Sugita et al. | 463/36 |
| 6,167,298 A | * | 12/2000 | Levin | 600/545 |
| 6,657,183 B2 | * | 12/2003 | Yamamoto et al. | 250/221 |
| 6,795,724 B2 | * | 9/2004 | Hogan | 600/545 |
| 7,239,903 B2 | * | 7/2007 | Eda | 600/310 |
| 2003/0023319 A1 | * | 1/2003 | Andersen et al. | 623/24 |
| 2003/0093129 A1 | * | 5/2003 | Nicolelis et al. | 607/45 |

FOREIGN PATENT DOCUMENTS

| | | |
|---|---|---|
| JP | 7-124331 | 5/1995 |
| JP | 09-149894 | 6/1997 |
| JP | 9-149894 | 6/1997 |
| JP | 2000-116625 | 4/2000 |
| JP | 2000-172407 | 6/2000 |
| JP | 2000-325319 | 11/2000 |
| JP | 2002-119511 | 4/2002 |
| JP | 2002-172106 | 6/2002 |
| JP | 2002-224089 | 8/2002 |
| JP | 2004-141258 | 5/2004 |
| JP | 2005-13464 | 1/2005 |

OTHER PUBLICATIONS

"Spatial and temporal analysis of human motor activity using noninvasive NIR topography", Medical Physics, Dec. 1995, Am. Assoc. Phys. Med., vol. 22, No. 12, Maki et al, pp. 1997-2005.

(Continued)

*Primary Examiner* — Brian Casler
*Assistant Examiner* — Michael N Fisher
(74) *Attorney, Agent, or Firm* — Antonelli, Terry, Stout & Kraus, LLP.

(57) ABSTRACT

The present invention is helpful in improving stability of repeated measurement and can be applied with high reliability for operations of devices for measurement based on brain functions. A module 801 (a sampler) receives measurement data at each of the measuring points based on information of cerebral blood amount sent from an input unit. The information data accumulated in this sampler are processed by filtering at a secondary agent 803 and a tertiary agent 804 and are analyzed. The synthesizer 802 integrates output information of each agent by weighted linear sum and transmits the data as an output data 602 to the device and operates the device.

2 Claims, 21 Drawing Sheets

OTHER PUBLICATIONS http://ww.hitachi.co.ip/New/cnews/month/2005/09/0926.html, "A product marketed in the name of Kokoro Gatari" (Mind-Talker); A yes/no judging device for the patients of ALS, who cannot move own body.

V.N. Vapnik, "The Nature of Statistical Learning Theory, 2nd Ed.", Springer 2000.

* cited by examiner

FIG. 13

| Setting number | Setting time | 1301 |
| --- | --- | --- |
| Task number | Task time | 1302 |
| Agent 1 | Evaluation E(I) | 1303 |
| Agent 2 | Evaluation E(I) | |
| ... | | |
| Agent N | Evaluation E(I) | |
| Synthesizer output | Evaluation E(I) | 1303 |

US 8,175,686 B2

EXTERNAL CONDITION CONTROL DEVICE BASED ON MEASUREMENT OF BRAIN FUNCTIONS

FIELD OF THE INVENTION

The present invention relates to an external condition control device based on measurement of brain functions. In particular, the invention relates to a biological (living body) control device, in which an output signal of an information input device based on a bio-optical measurement method is used as an input signal for an external device to performs various types of control operations.

BACKGROUND ART

An external condition control device based on measurement of brain functions (also called "biological control device") is operated by opto-biological measurement method and biological input device, and it is applied for operation of alarm device to give warning on physical conditions of a subject on test such as sleeping or decline of attentiveness and for the control of various types of devices without using button, mouse or handle for the control of the devices in the external condition to match the state of consciousness and unconsciousness of the subject, judgment of skillfulness in rehabilitation, the result of learning or displaying of sensing and thinking of the subjects including infants, adults or animals or for detection of lie.

In the past, various types of input devices such as button, keyboard or mouse have been used to operate information processing devices, video game devices, household electric appliances, audio-visual devices, transport devices, etc. However, the input devices operated by manual operation of a human operator may temporarily hinder the attention concentrated on another input operation or may decrease the feeling of the subject (i.e. an operator of a device or a player of video game) as if he or she were actually present at the site. Also, difficulties may arise when a physically handicapped person operates the device. In this respect, attempts have been made to control the device by using information directly obtained from the brain of the subject (i.e. the user).

As for the means for obtaining control information as described above by directly measuring the brain functions, studies have been performed to directly pick up electric signal by placing electrode into brain of the subject. However, in the measurement method, by which it is necessary to embed and bury an implant device by putting it into human body (invasive method), there is always a possibility to cause side effects (adverse effects). On the other hand, as a noninvasive method, i.e. as a measurement method not using the means such as needle or surgical knife to put into human body, various methods are known, e.g. positron emission tomography (PET), functional magnetic resonance imaging (fMRI), electroencephalography, etc.

The Patent Document 1 discloses a device, by which control information from brain of a subject based on brain wave is directly inputted into a controlled device. In the device disclosed in the Patent Document 1, the data of brain wave is directly inputted into an information processing device in a manner similar to the case where measurement is made by means of electrocardiogram, and it is attempted to control a computer—in particular, a video game device. By the direct input device to input the data from brain to a controlled device, even a patient with difficulties in motor functions can control the external device, and this may be helpful in promoting the return of the physically handicapped persons to direct participation in social activities.

Further, in addition to the techniques as described above, a new technique has been introduced by using near infrared spectroscopy. According to this method, the changes of a blood amount in a cerebral cortex associated with brain activities are measured at a multiple of points on the head of the subject, and the changes of blood amount are displayed (optical topography). This method has been used in practical application, and it is published in the Non-Patent Document 2.

As the techniques to disclose the background art in this field, the techniques disclosed in the Patent Documents 3 to 6 and the Non-Patent Documents 1 to 3 are known in addition to the Patent Documents 1 and 2 as given above. The details of the disclosures in these documents will be described later as necessary in connection with the problems to be solved by the present invention, the means for solving the problems, and in the description of the embodiment of the invention.

[Patent Document 1] JP-A-7-124331
[Patent Document 2] Japanese Patent No. 3543453
[Patent Document 3] JP-A-9-149894
[Patent Document 4] JP-A-2000-172407
[Patent Document 5] JP-A-2002-119511
[Patent Document 6] JP-A-2005-13464 (Opto-biological measuring device)
[Non-Patent Document 1] Maki, A. et al., (1995): "Spatial and temporal analysis of human motor activity using noninvasive NIR topography"; Medical Physics 22; 1997-20.
[Non-Patent Document 2] "http://www.hitachi.co.jp/New/cnews/month/2005/09/0926.html"; A product marketed in the name of "Kokoro Gatari" (Mind-Talker); A yes/no judging device for the patients of ALS, who cannot move own body"
[Non-Patent Document 3] Vapnik, V. N.: "The Nature of Statistical Learning Theory, 2nd Ed.", Springer; 2000.

DISCLOSURE OF THE INVENTION

Referring to FIG. 1 to FIG. 5, description will be given below on a basic technique of an external condition control device based on measurement of brain functions. In order to elucidate the problems in the present invention, each of FIG. 1 to FIG. 5 also represents basic arrangement to describe embodiment of the present invention. FIG. 1 is a schematical drawing to explain a measuring method of the external condition control device based on measurement of brain functions. It also represents arrangement of device for the measuring method as disclosed in the Patent Document 2 or the Non-Patent Document 1. FIG. 2 is a drawing to explain a path 201 of a light beam propagated between a holder 107 for fixing an optical fiber 104 connected to a light projector 103 and a holder 107 for fixing an optical fiber 106 connected to a light detector 105.

A subject on test 101 wears a helmet (probe) 102 for measurement. This helmet 102 comprises an optical fiber 104 connected to a light projector 103 typically represented by a light emitting diode, a semiconductor laser, or a lamp, and it also comprises an optical fiber holder 107, which includes an optical fiber 106 connected to a light detector 105 typically represented by an avalanche photo-diode or a photomultiplier.

A tip 108 of the optical fiber such as the optical fibers 104 and 106 is brought into contact with scalp of the subject through hairs of the subject 101. This is because light transmission efficiency is decreased if the hair is interposed between the fiber tip and the scalp. There are provided a plurality of the light projectors 103. These are designed as multi-channel system where output light intensity at each moment is managed and controlled by a control device 109. The control data is transmitted to a signal processing device 111 connected to the light detector 105 via a transmission cable 110. The data may also be used to estimate the changes of light intensity, which passes inside the body of the subject. Reference numeral 112 denotes an information processing device with an input unit represented by a personal computer or a work station. The details of the control operation are transmitted to the control device 111 via the transmission cable 113, and the results of the processing are incorporated in the device and are analyzed. The results of the analysis are displayed on a display screen 114. Reference numerals 115 and 116 represent keyboard and mouse, which are input devices of the information processing device 112 respectively.

Each of the holders 107A and 107B is fixed on a helmet 102, which is fitted to the head of the subject 101 as shown in FIG. 1, and tips of the optical fibers 104 and 106 are brought into contact of the scalp of the subject. FIG. 2 schematically shows typical structure of human brain. The brain structure consists of a scalp 202, a skull 203, a cerebrospinal fluid layer 204, a cerebral cortex 205, etc. It is known that these biological (living body) tissues have optical scattering property and absorption property, and, in particular, that the skull 203 has high light scattering property. For this reason, the light beam projected from the light projector 103 is scattered by this scattering property and the intensity of the light will be gradually lost due to light absorption property. The holders 107 are disposed at a distance of about 30 mm from each other in grid-like arrangement.

When the holders are disposed with such distance from each other, the light beam projected from the optical fiber 104 connected to the light projector 103 is propagated along a path with a form 210 shown in the figure while the light advances with repeated scattering and absorption into the living body tissues. Then, the light reaches the optical fiber 106 connected to the light detector 105 and is detected. For this measurement, near infrared light (with a wavelength of 600 nm to 900 nm) with high transmission property to the living body tissues is used. In the figure, reference numeral 211 denotes an area where the concentration of bio-metabolite represented by blood amount is increased in association with the activities of the brain in the cerebral cortex 205.

Blood comprises various types of substances. Among these substances, it is known that hemoglobin (oxygenated hemoglobin and de-oxygenated hemoglobin) absorbs the near infrared light used in the measurement. As a result, it is known that the intensity of the detected light is attenuated when the blood amount increases. Specifically, by detecting the changes of the light, the changes of blood amount can be estimated. Detailed description on this estimating method is given in the Non-Patent Document 1.

The remarkable feature of the opto-biological measuring device described in the Non-Patent Document 1 is that the light projector and the light detector are arranged two-dimensionally on the scalp of the subject. Thus, it is possible to visualize the distribution of the changes of blood amount caused in association with brain activities.

FIG. 3 is a drawing to explain disposed positions 301 (shown by open circles in the figure) of the optical fiber holder 107A connected to the light projector 103 and disposed positions 302 (shown by black circles in the figure) of the optical fiber holder 107B connected to the light detector 105. These holders for light projection and light detection are spatially arranged with a distance of about 30 mm from each other. According to FIG. 2, thickness of the form 210 of the light path reaches the highest value at a position 303 immediately below a middle point between the disposed position 301 of the optical fiber holder 107A connected to the light projector 103 and the disposed position 302 of the optical fiber holder 107B connected to the light detector 105. As a result, it is known that the sensitivity to the changes of blood amount reaches the highest value at this middle point. In this sense, this middle point (shown by the mark X in the figure) is called a sampling point 303, and it is defined as a point, which gives position information of the changes of blood amount as detected via a pair of the optical fibers.

In FIG. 3, the disposed positions 301 of the optical fiber holder 107A connected to the light projector 103, the disposed positions 302 of the optical fiber holder 107B connected to the light detector 105, and the sampling points 303 are shown, but the reference numerals are given only on the representative two disposed positions and on the representative one sampling point. As it is evident from the fact that the disposed positions of the other holders and the other sampling points are also shown by the same open circles and black circles and the marks X respectively, in an example shown in FIG. 3, there are 24 sampling points in all by the arrangement of 8 light input points and 8 light detecting points. By using the information at each of these 24 sampling points, it is possible to visualize brain activities as shown in FIG. 4.

FIG. 4 shows an example of a topographic image obtained by spatially interpolating the changes of blood amount at each of the sampling points. By this image, it is possible to obtain spatial distribution of the changes of blood amount at a certain time point, and it is also possible to visualize average value of the changes of blood amount within a period of brain activities. As shown in FIG. 4, when the opto-biological measuring device is used, brain activities can be measured. Also, as shown in the figure, the distribution of the disposed positions of the optical fiber holders 107A for light projection and the disposed positions 302 of the optical fiber holders 107B for light detection as well as the sampling points 303 can be displayed in superimposed arrangement. As a result, it is possible to estimate the position of localized brain activities.

According to this measuring method, measurement can be made by using weak light when the subject wears the helmet. Thus, the subject can undergo the test with high safety and with free physical posture. Therefore, measurement can be made on a wide variety of human subjects from infants to elderly persons. For instance, in the functional magnetic imaging or in the positron emission tomography as used for the measurement in the past, the subject is not allowed to move during the measurement. In particular, in case of an infant, anesthetic or sedative had to be given in the past to prevent the infant from moving. In some of such cases, it is difficult to accurately measure the activation of brain activities. Also, regardless of whether the subject is an infant or an elderly person, the subject generally had to undergo the test within a limited space and without physical movement. This often leads to the problem where a condition mentally different from normal living condition is required. Brain wave can be measured in relatively stable condition but there is strong influence of electromagnetic wave. This means that electromagnetic shielding is needed to ensure stable measuring operation. In contrast, in the brain function measuring device using light, the test can be performed under relatively free external conditions and in free physical posture. As a result, the device according to the present invention can be used under the condition where the measurement has been difficult to perform by a conventional type brain function measuring device.

In the Patent Documents 3 and 4, examples to control external devices are described by a method to measure the changes of blood amount by using infrared light in cerebral cortex. In these Patent Documents, human brain is divided into different cell structures as shown in Brodmann's brain map. Further, these are based on the knowledge that each of the areas is in charge of different function. For instance, when the brain is seen from lateral direction, voluntary movement (such as the movement of hands, fingers, feet, etc.) is controlled by parietal region of the head. The area related to sensing or visual perception is occipital region, and an area related to language is an area located at the left half of the brain, and these functions are controlled by each of these areas respectively. By using the functions of the measuring device, an intention conveying device is proposed for a patient, who cannot activate muscles any more due to nerve diseases (Non-Patent Document 3 and the Patent Document 5). This device is to measure the changes of blood amount when the subject calculates mentally or sings a song in mind by applying near infrared spectroscopy to two points in the forehead.

A method called "support vector machine" is known as a method to be used when condition judgment should be made according to the data of a plurality of channels. Description will be given now on this method based on the details described in the Non-Patent Document 4. It is supposed here that learning data (x, y) as many as N as expressed in combination of a vector x with d-dimensional information and a discrete value y to indicate a value {+1, −1} is present to give a learning rule. FIG. 5 is a schematical drawing to explain the situation. Each of data 501 as indicated by an open circle in FIG. 5 represents a learning condition 1, which is represented as y=1. Each of data 502 represented by a black circle indicates a learning condition represented by y=−1.

In this case, in order to separate the learning data 1 from the learning data 2, a "D-1"-dimensional hyperplane 503 (given by the mathematical equation 1) in FIG. 5 is defined so that optimal condition shown in the mathematical equation 2 can be satisfied.

[Mathematical equation 1]

$$f(x) = \sum_{j=1}^{d} w_j x_j + b \quad \text{Equation 1}$$

[Mathematical equation 2]

$$\min_{k=1 \ldots N} \frac{|wx_k + b|}{\|w\|} = \min_{k=1 \ldots N} \frac{1}{\|w\|} \quad \text{Equation 2}$$

This is the same as the definition of a hyperplane so that distances from two groups will be equal to each other. In case it is not possible to separate by "D-1"-dimensional plane, the following definition is given by using positive slack variable (soft margin). Also, a method is known, according to which a new Hilbert space is prepared by conversion formula and optimization is performed to apply support vector machine in this space (kernel trick).

As disclosed in the Patent Documents 1 and 2, when a multiple of sensors are installed using a helmet, the types of brain activities, which can be measured, are increased. As a result, the degree of freedom for the device control is increased. However, when a multiple of sensors are installed on the helmet, all of the sensors do not necessarily fulfill the function when the subject wears the helmet at one time. For instance, if a piece of hair is interposed between contact tips 108 of the optical fiber cable, spectrum of the light is extensively absorbed at that point, and this may extremely aggravate the accuracy of the detector. To avoid such trouble, a method is proposed in the Patent Document 5, according to which the subject wears the helmet while confirming the light intensity on each of the sensors.

When the opto-biological measuring device, which will be effectively utilized in various applications, is used for the purpose of driving the external devices or for communication, one of the most important problems is the stability of the measurement and the analyzing means. If the helmet can be worn easily by the subject and the measurement can be made within short time, it would be turned to a device, which does not give much burden on the side of the user.

However, when it is attempted to control the device by such signal, an important problem for practical application of this technique is that there are high individual difference is high in the reaction signal of the structure of human brain and in the instability of the sensors. The examples of such individual differences are: thickness of skin in individual subject, difference of disposed positions of each piece of hair, difference of physical size and shape of the skull in individual subject, geometrical error of the boundaries of the area where brain functions are localized, difference of blood vessel structure and the difference of reaction in the changes of blood amount, etc. Also, even when the same problem such as the same calculation may be given in the same manner, some subject may give a solution visually, while some other subject may seek the solution by sound. For this reason, there may be difficulties if a reaction pattern, which is always adaptable to a certain subject, is determined in a uniform and standardized theory.

Depending on the condition of installation of the helmet 102 on the subject as shown in FIG. 1, there may be a case where accurate measurement cannot be made on a part of the measuring points. Such case is specially found when contact portions of the optical fiber holders 107A and 107B are attached to such points where there are many pieces of hair. Also, depending on the re-wearing of the helmet 102, the positions of the light sources to be installed may be slightly different or the degree of impact on the scalp by the helmet 102 may be slightly different, and some changes may be caused in the accuracy of the signal. Further, depending on the posture of the user, the influence of the pulses on the changes of cerebral blood amount may vary.

Because the conditions such as the thickness of the skull or pigment condition on the skin may differ at each of the measuring points, the degree of absorption of the light at the areas such as epidermis or skull bone differ according to each individual subject or at each measuring position. For this reason, when the near infrared spectroscopy is used, it is not possible to directly compare the data detected at each measuring point as an absolute value. In the operation of optical measurement, the moment when the measurement is started is defined as zero point when the measuring device is actually installed, and a value of relative change from such condition is regarded as information on the measurement result. In the current technique, which cannot perform perfect measurement and estimation on the path of the light, which passes inside human body, there are always difficulties to stably judge the conditions of installation of the helmet based only on the absolute value of the measurement.

From the reasons as described above, variations may occur for each individual subject and for each measurement operation in the accuracy of measurement or in the element relating to the error. For instance, there may be such an element that reaction is very likely to occur due to the localization of brain functions at a certain measuring point, or there may be such an element that reproducibility of the accuracy to detect the reaction may differ from each other. Specifically, there are many measuring points where it is difficult to perform measurement because the conditions of installation of the optical input/output device (the optical fiber holders 107 in FIG. 1) tend to be worse although strong reaction is indicated and measurement can be made correctly in normal case. There are also many measuring points where the measured reaction is weak but the installation condition of the device 107 is always stable. Because of the variations of reliability at different measuring points, it is difficult to maintain the stability for condition judgment by uniform and simple application of the existing technique and means such as the support vector machine.

It is an object of the present invention to provide an external condition control device based on the measurement of brain functions, by which it is possible to improve the stability in the repetition of measurement operations and to increase the reliability.

According to the present invention, various types of information collected from each of the sensors are divided to individual information processing modules and are processed independently from each other, and the data to reflect localized functions or information on pulses are reflected independently from each other. For each element of the information processing modules, the repetition of reliability accuracy for each installation and the intensity of detection of the signal to cope with introspective activity of the subject are analyzed, classified and controlled, and various types of information of each individual subject are additionally stored in a medium. In so doing, the propagation of malfunction of a single sensor to the entire system can be avoided, and the weighting to contribute to the final output of information by the modules is changed over to match the reliability accuracy derived from the result of checking as to whether the modules contribute to the final output of information as to whether each of the modules is correctly fulfilling the functions. Or, instruction is given to the user to change the task.

According to the invention, it is possible to differentiate whether it is caused by the problem associated with the execution of the theme or it is caused by the contact of the device even when adequate signal cannot be obtained in comparison with the measurement in the past, and it is also possible to make selection of adequate introspective theme, which should be carried out under the current condition. Further, it is possible to prepare interface conditions to induce stabler behavior and to give the data to the subsequent measurement conditions by maintaining and increasing the learning parameters for long term based on the past record of individual subject for each component of functional elements.

BRIEF DESCRIPTION OF THE DRAWINGS

FIG. 13 is a table to show examples of data where information data in the past are accumulated;

BEST MODE FOR CARRYING OUT THE INVENTION

Description will be given below on embodiments of an external control device based on bio-optical measurement according to the present invention by referring to the attached drawings.

Embodiment 1

Figure 1:
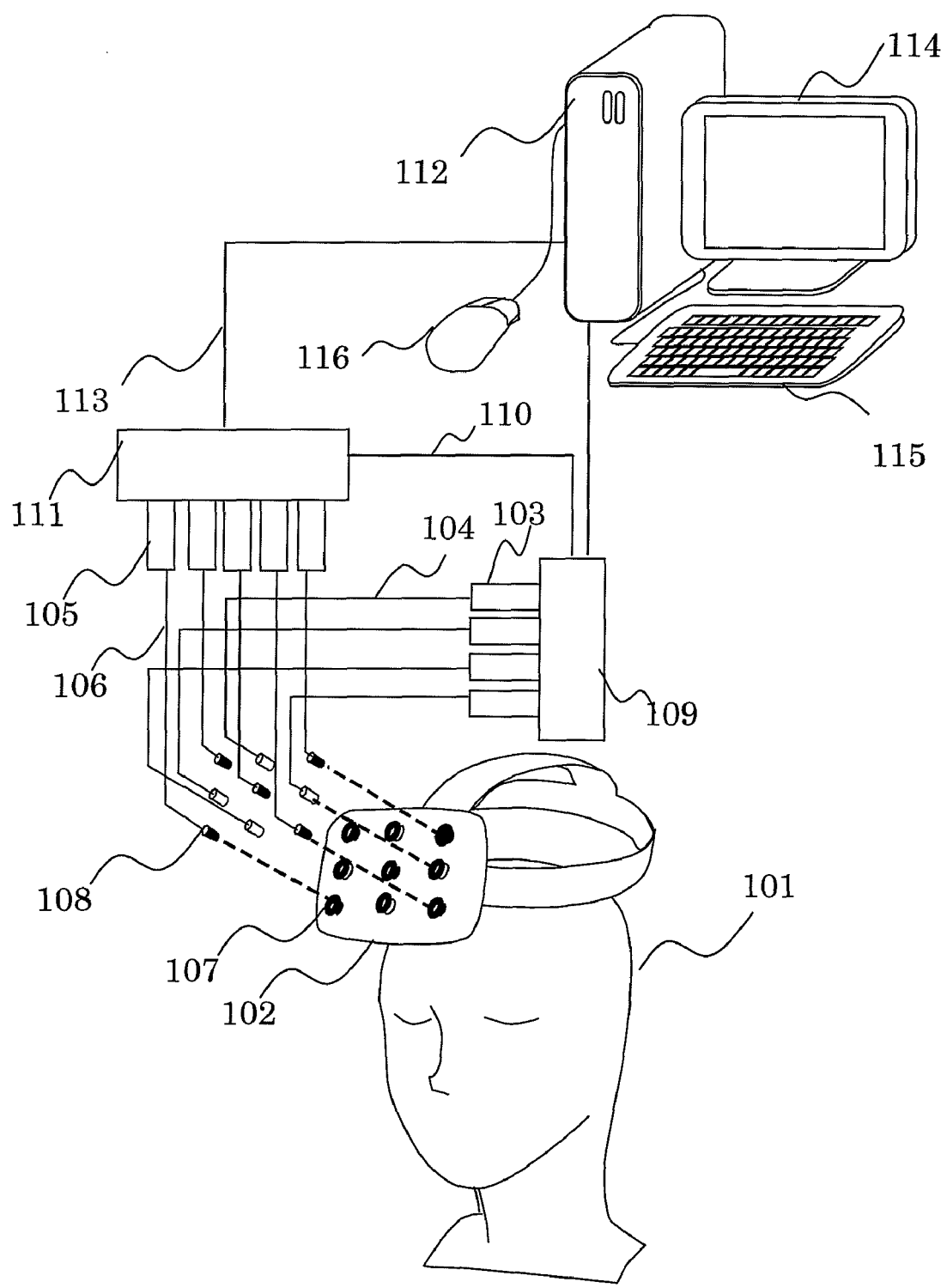
FIG. 1 is a schematical drawing to explain an example of arrangement of a measuring device in an external condition control device based on measurement of brain functions.
Figure 2:
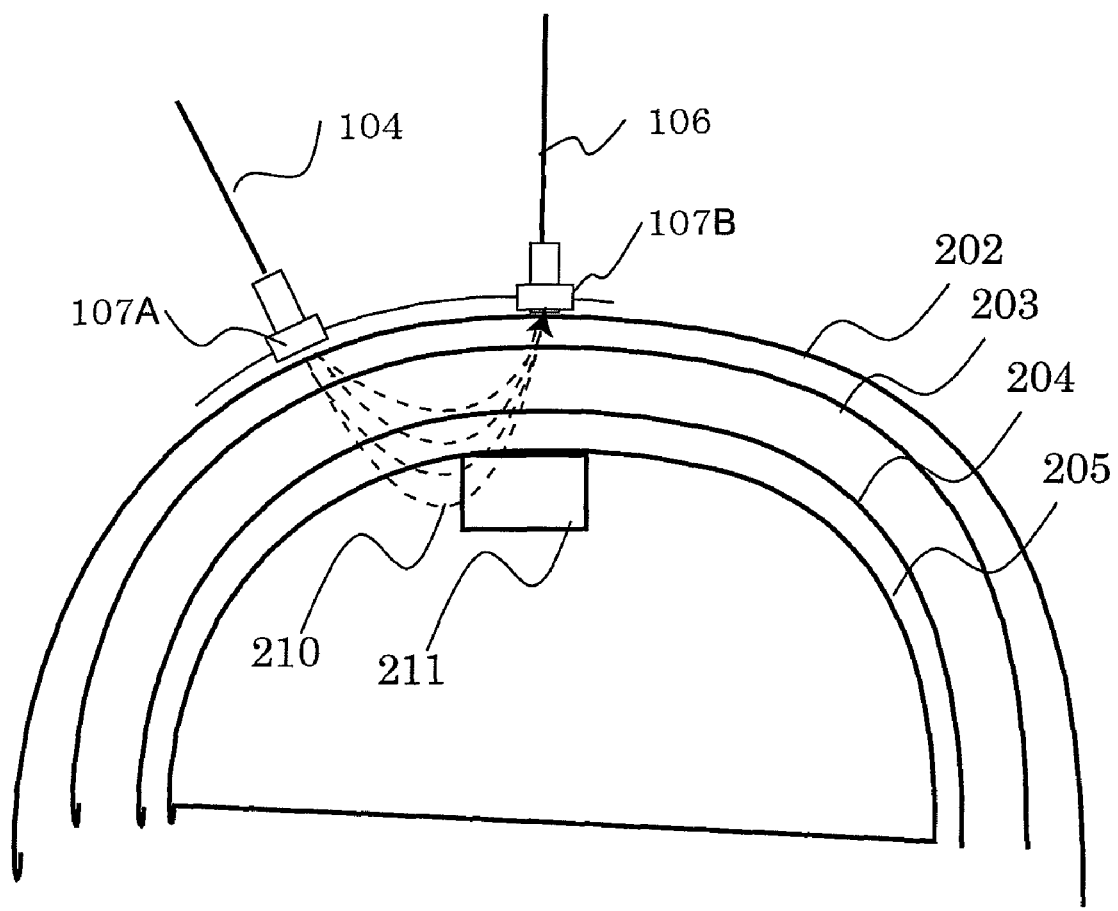
FIG. 2 is a drawing to explain a path of a light beam which is propagated between a holder for fixing an optical fiber connected to a light projector and a holder for fixing an optical fiber connected to a light detector as shown in FIG. 1.
Figure 3:
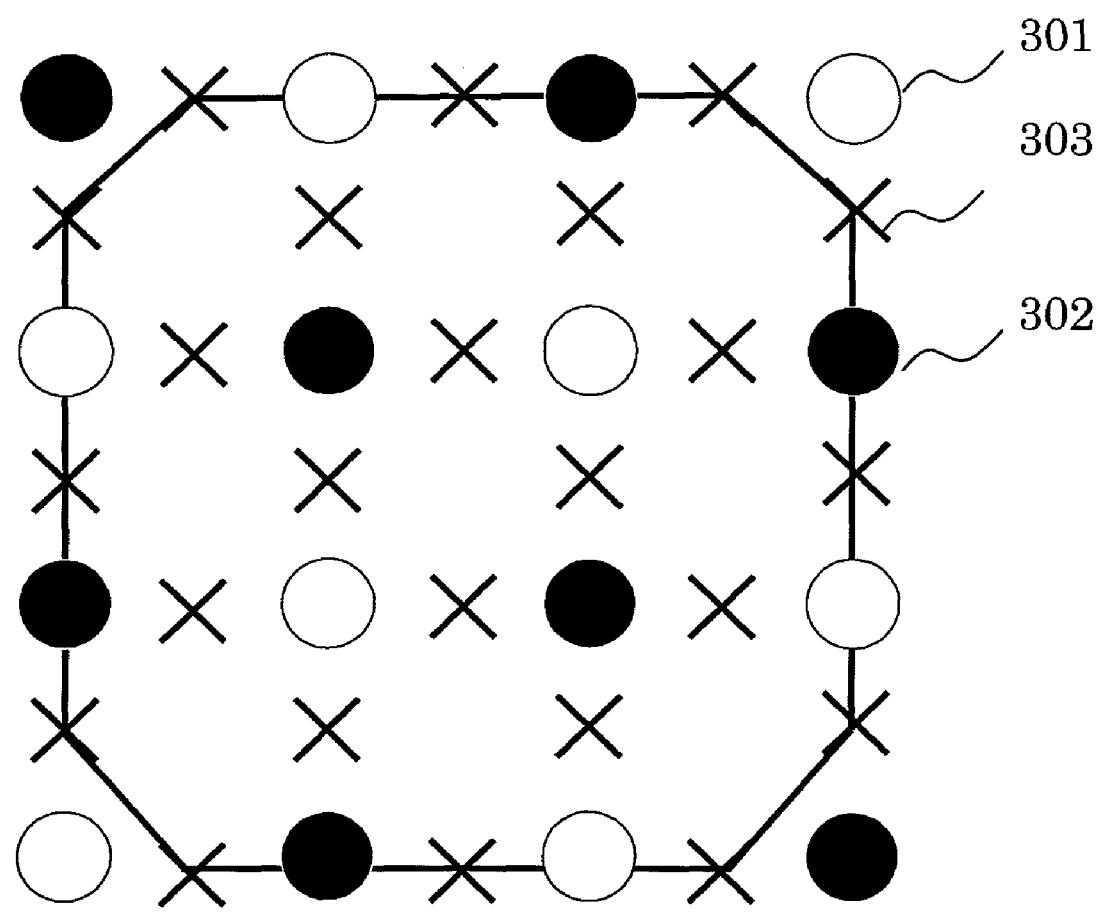
FIG. 3 is an illustration to explain disposed positions of an optical fiber holder connected to the light projector and disposed positions of an optical fiber holder connected to the light detector.
Figure 4:
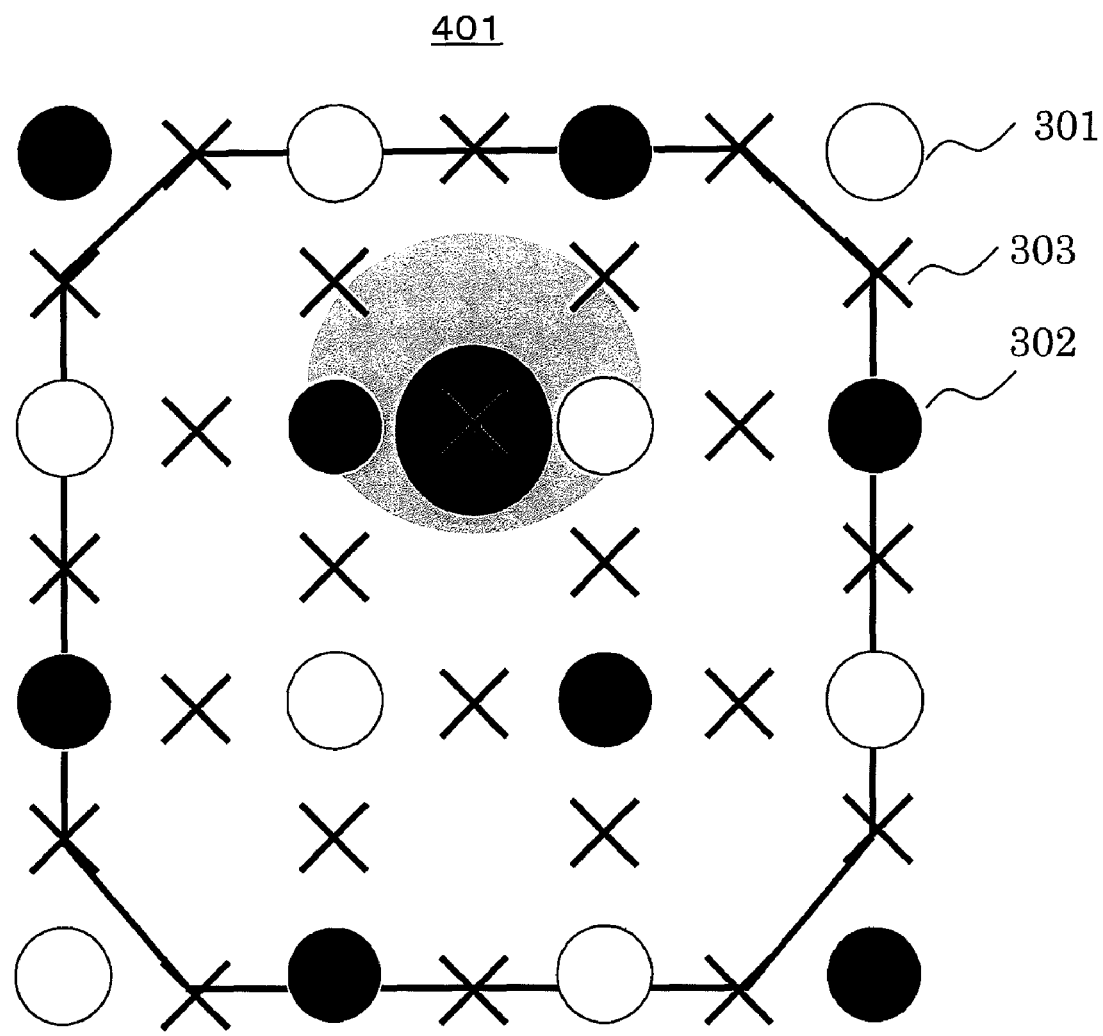
FIG. 4 is a drawing to explain an example for specifying points of changes of blood amount pattern according to a plurality of laser beams and sensors disposed in grid arrangement.
Figure 5:
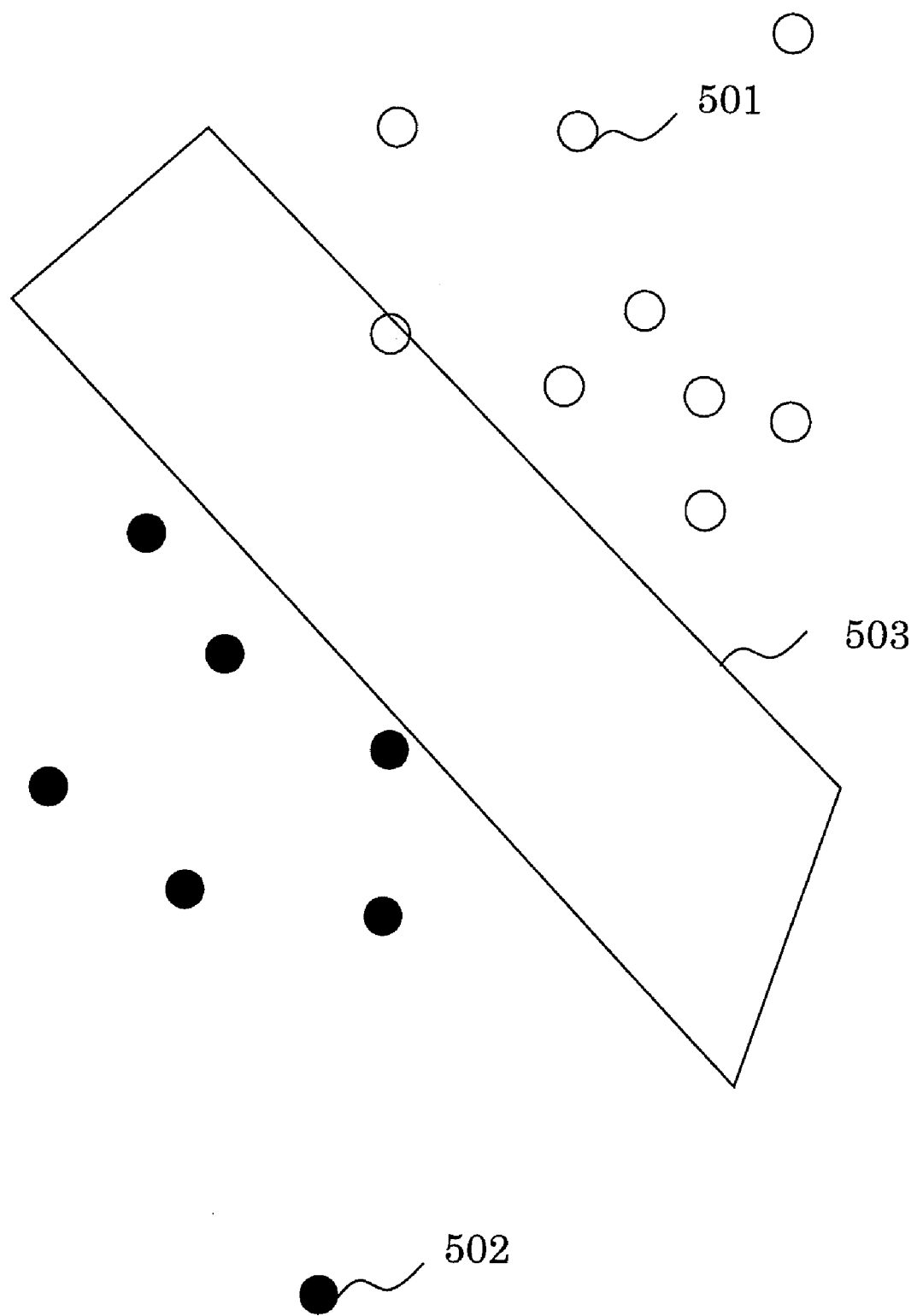
FIG. 5 is a conceptual drawing to represent a procedure to separate multi-dimensional information in linear configuration.
Figure 6:
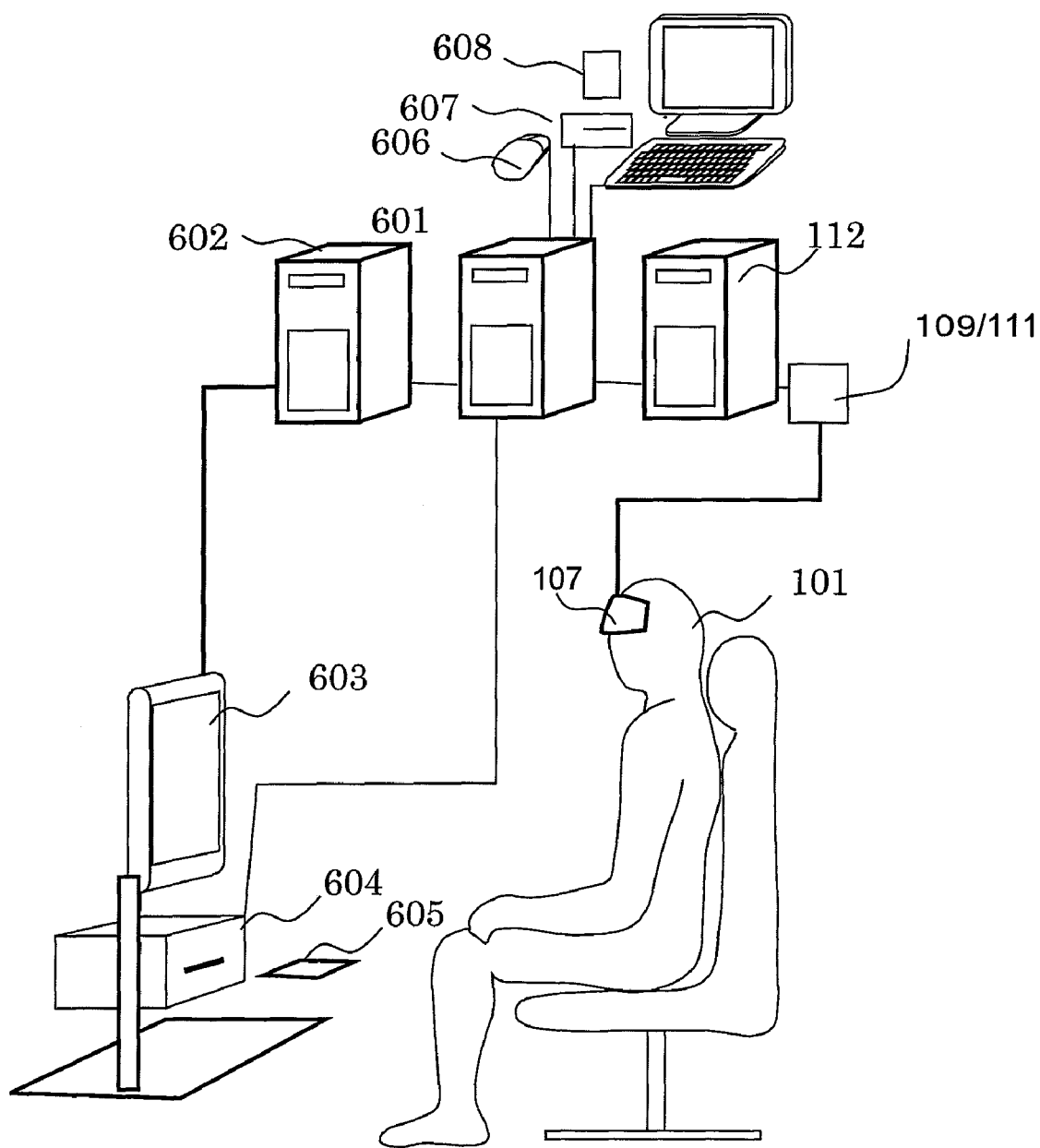
FIG. 6 is a schematical drawing to show Embodiment 1 of the external control device based on the bio-optical measurement according to the present invention.

FIG. 6 is a schematical drawing to show Embodiment 1 of an external control device based on bio-optical measurement according to the present invention. The component element with the same function as shown in FIG. 1 is referred by the same symbol. The system of calculation processing mechanism as shown in Embodiment 1 comprises information processing devices including an input unit 112, an information processing unit 601, and an output unit 602. These information processing devices are mutually connected to a network and can give and take input/output results to and from each other. As the information processing devices of this system, various types of general-purpose calculation devices such as a personal computer (PC) as widely known and a built-in type microcomputer module can be used.

It is also possible to design so that processing of the input unit 112, the information processing unit 601, and the output unit (output module) 602 can be carried out as software modules in the same information processing device. To facilitate the explanation on the functions, these are shown in form of individual information processing devices in the present embodiment. Also, a screen monitor 603 to give the results of the output unit (output module) 602 or to indicate a demand from the information processing unit 601 is disposed in front of a subject on test 101. Further, a medium 605 for recording the details of measurement history of the subject 101 and a reader 604 for delivering the details to the information processing unit 601 are provided.

Also, the media 608 contains information on a procedure to combine the modules to be used in the information processing unit 601, and the information is read from the reader 607 when the information processing device 601 is started. Further, this information can be changed by a manual input interface 606.

The system of Embodiment 1 is operated by changing the following two modes: a learning phase mode and a real-time operation phase mode. Description will be given now on operating procedure of the entire system of this embodiment by referring to the flow chart shown in FIG. 7. In the measurement phase mode, the present system measures the conditions of cerebral blood amount when the subject on test is engaged with a given theme and generates parameters to use the conditions in the real-time operation mode. In the real-time operation mode, the theme, with which the subject is currently engaged, is estimated by using the parameters obtained in the cerebral blood amount measured and the parameters obtained in the learning phase mode, and operation is executed to the environmental condition, to which the subject is exposed. The subject changes the theme by understanding the conditions of the environmental operation and carries out the act in question. Also, in the real-time operation mode, the parameters are adjusted again depending on the degree of performance to this act. Now, description will be given on behaviors of the device in each of these modes.

The operation of Embodiment 1 is started (Step 701), and the user 101 wears a helmet 107 of the optical measuring device, i.e. a sensor, on his or her head (Step 702). Then, operation of each agent is confirmed in the learning phase mode (Step 703) and an amount of reaction of the agent is estimated from the degree of accomplishment of the current reaction (Step 704). Depending on the results of the estimation, a suggestion is given to the user to change the task or to re-install the optical fiber holder (also called "probe holder") 107 (Step 705). The user 101 decides whether to re-install the optical probe holder 107 according to the suggestion or to select the task to be executed and is shifted to the real-time operation phase mode (Step 706). Description will be given on the details in each of these steps.

In the information processing device 601, an algorithm element is stored as a program, by which it is decided to use a value of the change of cerebral blood amount at each site of the brain sent from the optical probe holder 107 as an input signal and to convert it to an input value of the output module 602. A program of feedback operation to adjust the parameters in the measurement phase mode and a program to be used in the output module 602 in the real-time operation phase mode are provided, and the calculation module is used in common in these two types of modes. First, description will be given on the details of calculation processing algorithm, which is executed in the information processing unit 601.

Figure 8:
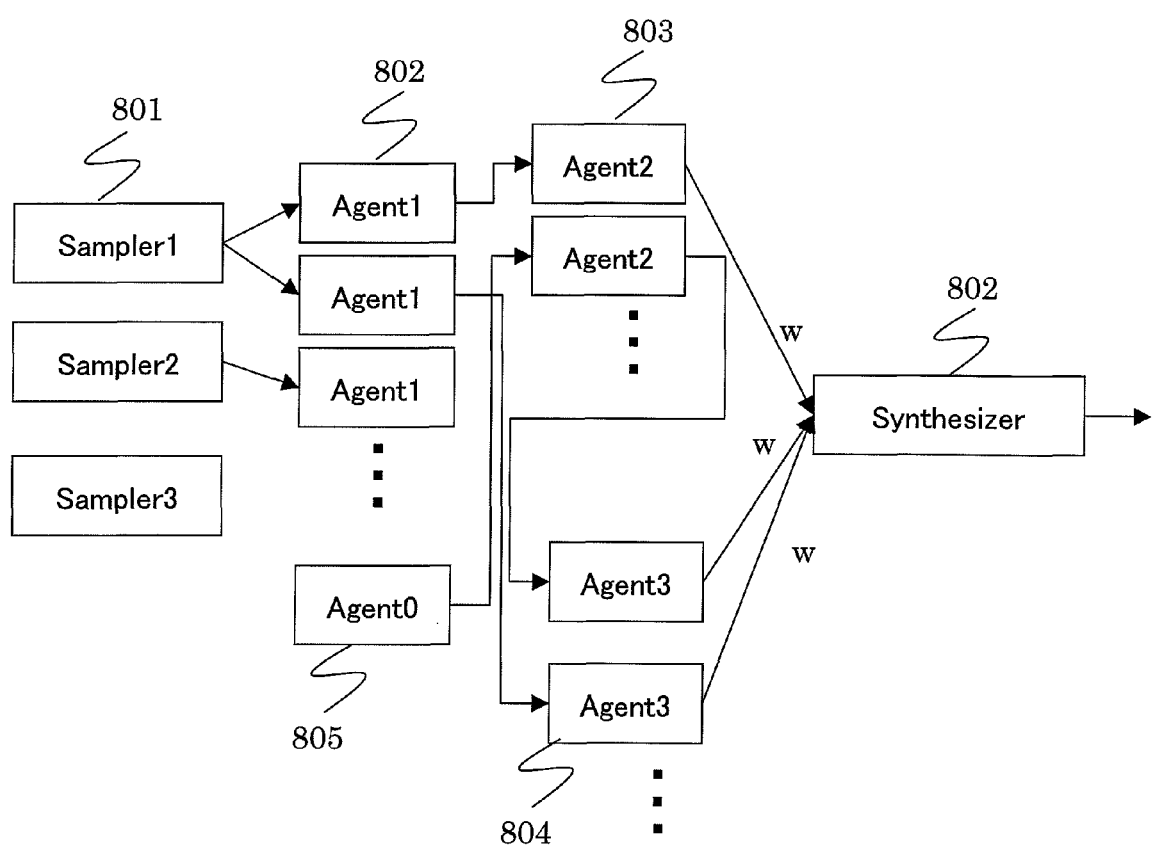
FIG. 8 is a block diagram to show system arrangement to explain a module structure to carry out information processing.

FIG. 8 shows system configuration to explain the structure of modules to carry out the information processing, and it schematically shows the modules, which constitute the processes of the information processing as described above. This system is composed of three component elements. A module 801 receives measurement data at each measuring point from the information transmitted from the input unit 112. Also, it has a function to maintain and store the values in the past. Hereinafter, this module 801 is called "a sampler". Analyzing units 803 and 804 are the units to filter the information stored in the sampler.

The modules (802, 803, 804 and 805) as described as "agents" in FIG. 8 are mounted on the program as various types of filter units. Hereinafter, these are referred as "agents". Further, an integration unit 805 integrates the output information of each agent by weighted linear sum and transmits it to the external output unit 602 or uses it for calculation of parameter adjustment. Hereinafter, this unit is referred as "synthesizer". The total connection system is designed in a tree structure similar to a multi-hierarchical neural network. Input/output of each agent module is a time-series data, and it consists of filtering processing of the functions specifically adapted for biological measurement of cerebral blood amount and general-purpose filtering calculation processing.

First, the agent module to perform the filtering processing will be described. Each of the agents 802, 803, 804 and 805 is a unit module, which receives the time-series information changing at real time. Then, the information is converted by a certain given algorithm, and the converted time-series information is outputted. Each of these agents 802, 803, 804 and 805 uses the time-series information updated at real time as an input, and the results of processing are constantly outputted. Also, each of these modules can have a constant as predetermined, and optimization processing is performed through changing and/or adjusting by the feedback from the synthesizer or by manual inputting from the manual input interface 606.

The agents are managed and controlled by classifying them to a primary agent 802, a secondary agent 803, a tertiary agent 804 and a pseudo-agent 805, depending on the functions. A module, which directly processes and outputs the time-series information of the change of blood amount at a certain measuring point is referred as the primary agent. The primary agent 802 can prepare data for each of the blood amount of oxygenated hemoglobin, the blood amount of de-oxygenated hemoglobin, the blood amount of total hemoglobin, and a value of blood amount obtained by subtracting the de-oxygenated hemoglobin from the blood amount of the oxygenated hemoglobin.

A module, which incorporates the results from a plurality of the primary agents and outputs the results of the processing according to a given algorithm, is referred as the secondary agent 803. The secondary agent receives the output from a plurality of other agents as its own input and processes it.

There is a module, which reflects the learning parameters obtained from the synthesizer and converts the results of the primary and the secondary agents to non-linear form and processes it so that the reaction corresponding to the change of introspective condition of the user can be easily separated. This module is referred as the tertiary agent 804.

Further, there is a module, which does not reflect the data from the cerebral blood amount directly stored in the sampler but which can use it as an agent module in pseudo manner on the calculation. This is referred as a pseudo-agent module 805.

Examples of algorithms used as the modules of the primary agent will be described below.

Frequency cut agent: This is a module, which cuts off high frequency component and low frequency component, extracts the information only on the components of the frequency concerned, and outputs it.

Running average agent: This is a module, which obtains the results based on the difference between running average of longer cycles and running average of shorter cycles and outputs the results.

Index running average agent: This is a module, which obtains the difference between index running average of longer cycles and index running average of shorter cycles and output the result.

Further, a pseudo-agent 805 is provided, which is driven based on the information from outside as inputted in synchronization with blood amount information of cerebral brain reaction. This is a module, which refers to the matters other than the reaction of cerebral blood amount, but which is processed according to the procedure similar to that of the primary module. The value to be outputted by these modules can be used as an input to the modules after the secondary module in the same manner as the primary agent. The examples are given below.

Stimulation indicating agent: This module exhibits such output behavior that it is turned to 1 from the time of starting of the theme and is turned to 0 at the completion of the theme in an external stimulation indicating device.

External pulse wave agent: This is an agent, which collects information on pulse waves from the positions other than the brain and reflects the result.

Movement acceleration agent: This is an agent, which outputs absolute value of an acceleration measuring device installed on the body of the user.

The module of the secondary agent receives the output of the primary agent or the pseudo agent as an input and converts it. Examples of algorithms, which can be used for the module of the secondary agent, are described below:

Finite difference agent: This is a module, which compares the output of the primary agent with a value outputted by the agent before a predetermined time period and outputs the difference.

Left-right difference agent: This is a module, which obtains the difference between an output of the primary agent at a given measuring position and an output of the agent at a measuring position on opposite side of the brain and outputs the result.

Average difference agent: This is a module, which obtains average difference of output values of the agent at all measuring positions with respect to the output of the primary agent at a certain measuring position, and issues the average difference as an output.

Divergence agent: This is a module, which obtains the difference between the output average value of the agent at the measuring positions around a certain measuring position and the output value of the primary agent at this certain measuring position.

Frequency analysis agent: This is a module, which extracts time-series data of absolute value of a specific component from the output of the agent measured by frequency analysis and outputs the result.

Pulse wave component agent: This is a module, which extracts the component regarded as a pulse wave from the output of the agent under measurement by frequency analysis in time series and outputs the result.

Examples of algorithms, which can be used in the module of the tertiary agent, are described below.

Function localizing agent: This is an agent, which collects the agents corresponding to channels to cover the scope of functions for each localized points of brain functions and extracts special features of each area through weighting by using a mechanism for processing multi-dimensional information such as a support vector machine on reaction information obtained through execution of the themes as given later and extracts special features of each function. A measurement area is defined as an area to cover N-area in Brodmann's brain map. Or, it is defined by the formulation of other brain function mapping such as the method 10/20 used in electroencephalography, or it is defined as an agent to cover language area in 90% of standard brain structure according to the functions estimated from the area. When a specific area of the agent is specified according to the function, a channel for each area to cover the entire area including individual difference is selected because there are divergences in brain functions and the shape of the head in each subject and there are individual differences such as the difference of head size in each subject. It is supposed, for instance, that the area of the functions of language area is included in the area R1 when measurement is made by installing the helmet on a certain subject. It is assumed, however, that the area R1 is near the average language area to be estimated by the method 10-20, and that it is an aggregation of the measuring points closely related to the language-related task. Also, it is assumed that the area of the functions of the language area is included in an area R2 when a probe 107 is installed on another subject. In this case, the area R1 does not coincides with the area R2. To cope with such case, the area is defined in the sum of sets when the devices are installed on a multiple of subjects in preliminary test, and this area is defined as the initial value of the function localizing agent.

Normalization agent based on standard deviation: This is a module, which calculates the running average and running standard deviation at all times with respect to the output of a certain agent. Then, the running average is subtracted from the current output result and this value is divided by the running standard deviation. The output result is then normalized by this agent.

Normalization agent based on pulse wave: This is a module, which constantly calculates amplitude of the component corresponding to pulse wave with respect to the output of a certain agent and normalizes the output by dividing the calculation result by this value.

Sigmoid conversion agent: This is a module, which applies the processing of sigmoid conversion as given in the mathematical equation 3 to the output of a certain agent and delivers the result by emphasizing the range of the values to be separated.

[Mathematical equation 3]

$$f(x) = \frac{1}{1 - \exp(-x)} \qquad \text{Equation 3}$$

AND agent: This is a module, which receives outputs of two agents and calculates the product of the two values and outputs it.

Highest value agent: This is a module, which receives output values from a plurality of agents and delivers the highest value.

Each agent module performs static filtering processing to be carried out sequentially and each of the agents simply repeats the operation to obtain an output value with respect to the input. By evaluating and calculating whether the result of this filtering processing agrees or not with the specific activity through the weighting procedure in accordance with the evaluation result by the synthesizer unit, it is possible to convert this result to a characteristic value to be used for the estimation of the introspective activity. The synthesizer unit multiplies each of the agents (agents as many as M in total) by the multi-dimensional weighted value "W=(w1, w2, . . . , wM)", and outputs the result to the output module. There are several types of this weighting procedure to correspond to the number of introspective tasks prepared as the example of the command.

The "weighted value" is stored in the medium 605, and it is read by the device 601 at the time of starting. In the initializing state, the learned parameters for an average user are stored. The results of measurement are accumulated each time the operation is carried out in the measurement phase mode to determine the coincidence of the activity with the behavior of the agent. By using the results, it is possible to make improvement of the weighted value to match the features of individual subjects and to have dynamic preparation of the weighted parameters to cope with the setting.

In the weighting procedure, it is also possible to prepare sets of the weighted values W to exceed the number C of the introspective tasks given as example of the command. Such example is effective in the case where there are too many dimensions of the variables and it is not possible to perform learning calculation within a reasonable time period if the learning calculation to obtain the compatibility with the tasks is carried out by using the output values of all agents. In such case, the learning module with higher accuracy can be prepared by performing the above learning calculation for each of subsets as determined in advance. The synthesis of the weighted value can be accomplished by mechanical learning procedure called "boosting".

Figure 9:
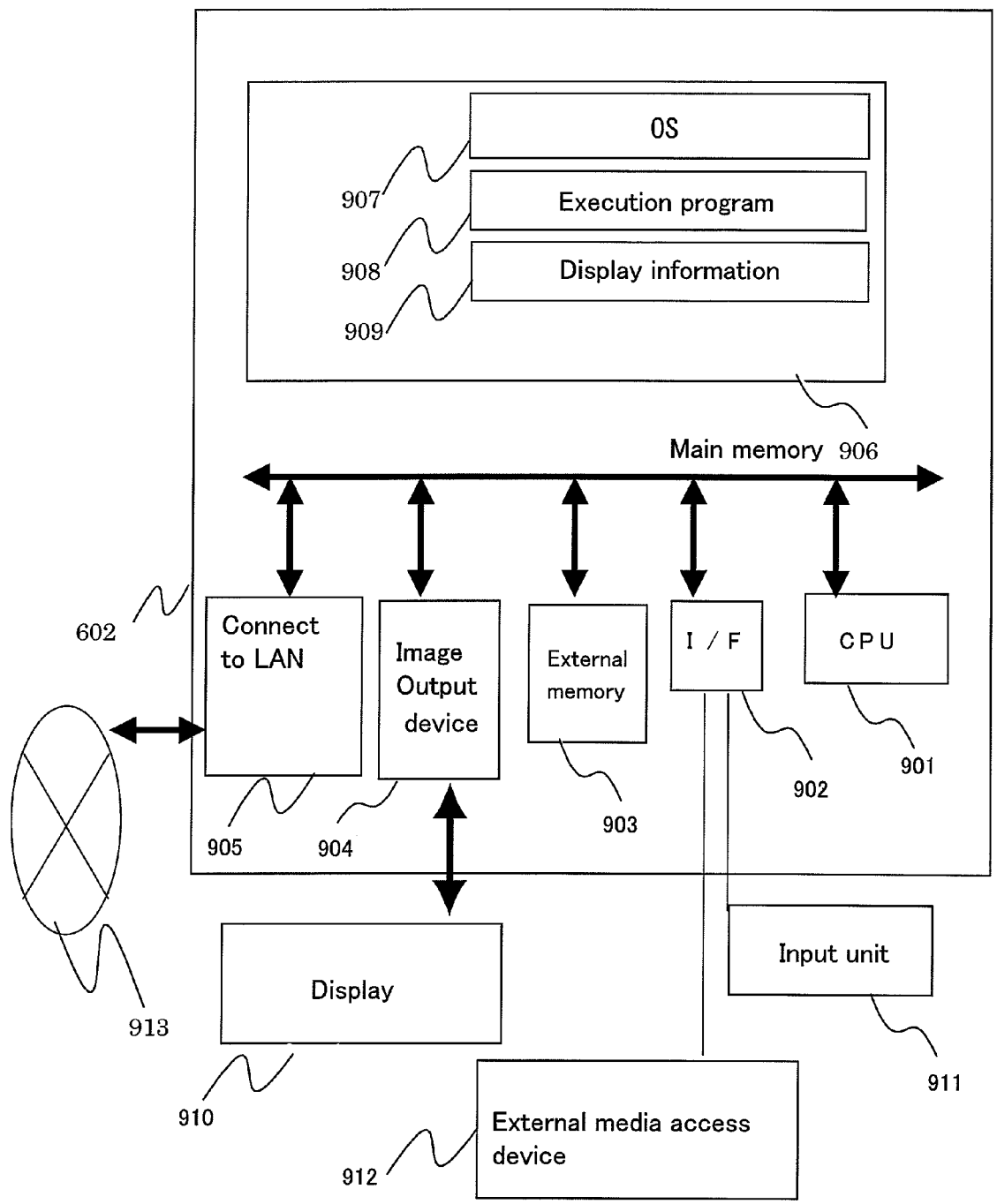
FIG. 9 is a block diagram of a general-purpose information processing device, which can be packaged and used.

The algorithm as described above is executed as a program module on the information processing device 602, which is shown in FIG. 6 as the output unit. FIG. 9 shows an example of configuration of a general-purpose computer, which can execute such program. A CPU unit 901 and an interface unit 902 to perform investigation processing, external storage devices (such as semiconductor media, optical media, magnetic media, etc.) to accumulate long-term data, an image processing device 904, and a device 905 and a main memory 906 to be connected to a local area network (LAN) are connected via the bus to mediate the data. At the time of starting, an operating system 907, an execution program 908, a display information resource 909, etc. are read from the external storage unit 903 to the main memory 906. A display monitor 910 can be operated from the image output device and the technique widely used for the mounting of a general type input device 911 represented by keyboard-mouse and a device 912 to gain access to external media can be applied. The technique to give and take the data to and from the information processing device 112 or the information processing device 602 via the local area network 913 is widely known. It is assumed here that the information processing devices 112, 601 and 602 as shown in FIG. 6 are the processing devices provided with such functions.

Figure 20:
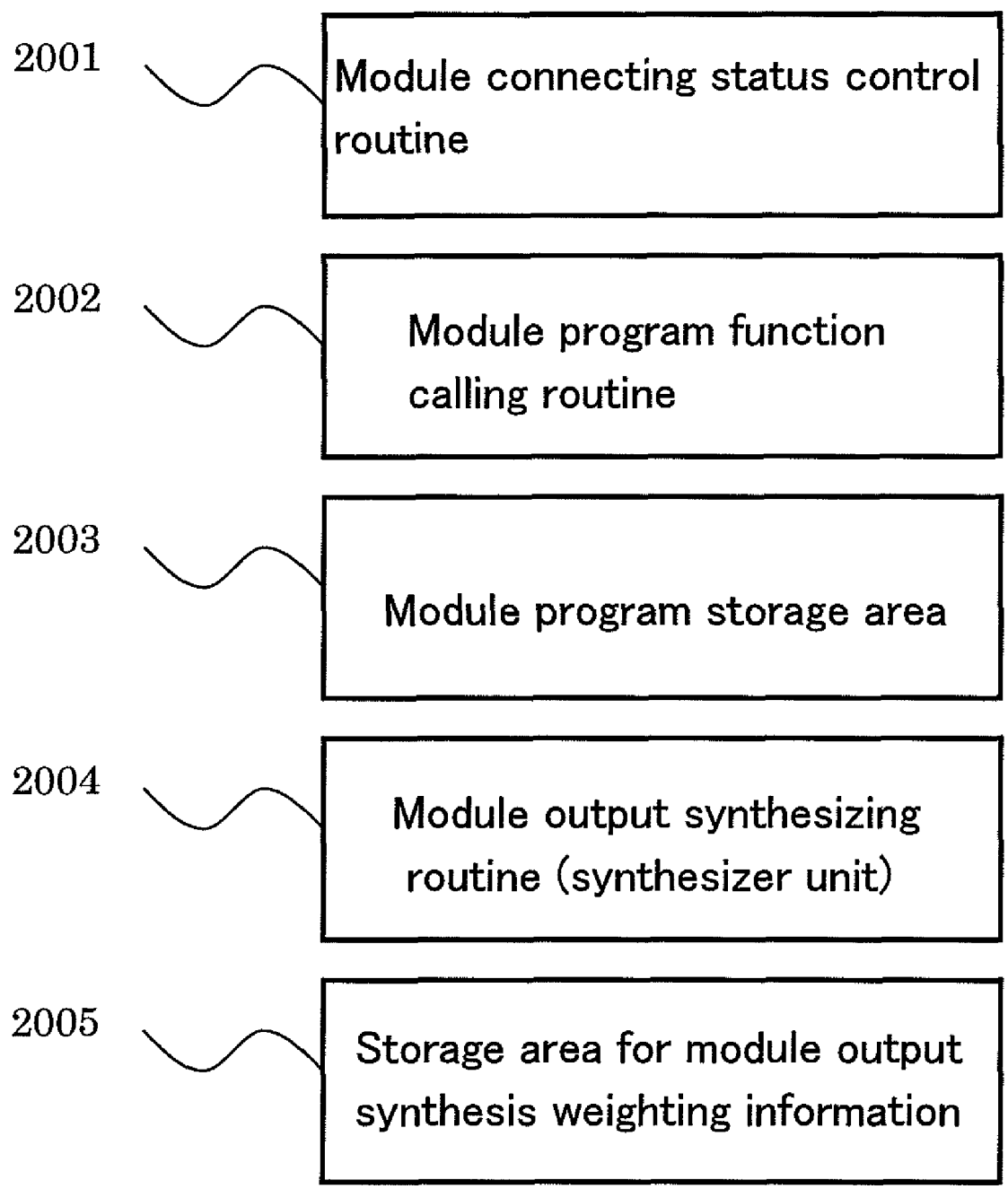
FIG. 20 is a block diagram to describe details of data for calling a filtering processing as shown in FIG. 8.

FIG. 20 is a block diagram to show the details of the data to call the filtering processing as shown in FIG. 8. The contents of these data are stored in the external storage memory 903, and the data are read on the main memory 906 at the time of execution as a part of the execution program 908. Reference numeral 2001 denotes a routine to manage and control the connecting condition of the module, and a tree structure as shown in FIG. 8 is maintained. Reference numeral 2002 represents a routine to call the function of the module program. By calling each of API functions of the module program according to the procedure as defined by this routine, calculation of the filtering is carried out. Reference numeral 2003 represents the module program in each of the module programs respectively. By setting the input relation as defined by the routine 2001 into this module program, actual behavior is determined. Reference numeral 2004 represents a routine, which sums up the outputs of the entire module expressed as the synthesizer unit as explained above. The output results of all evaluation functions can be obtained by finding linear sum based on the information of the weighting as stored in 2005.

Figure 21:
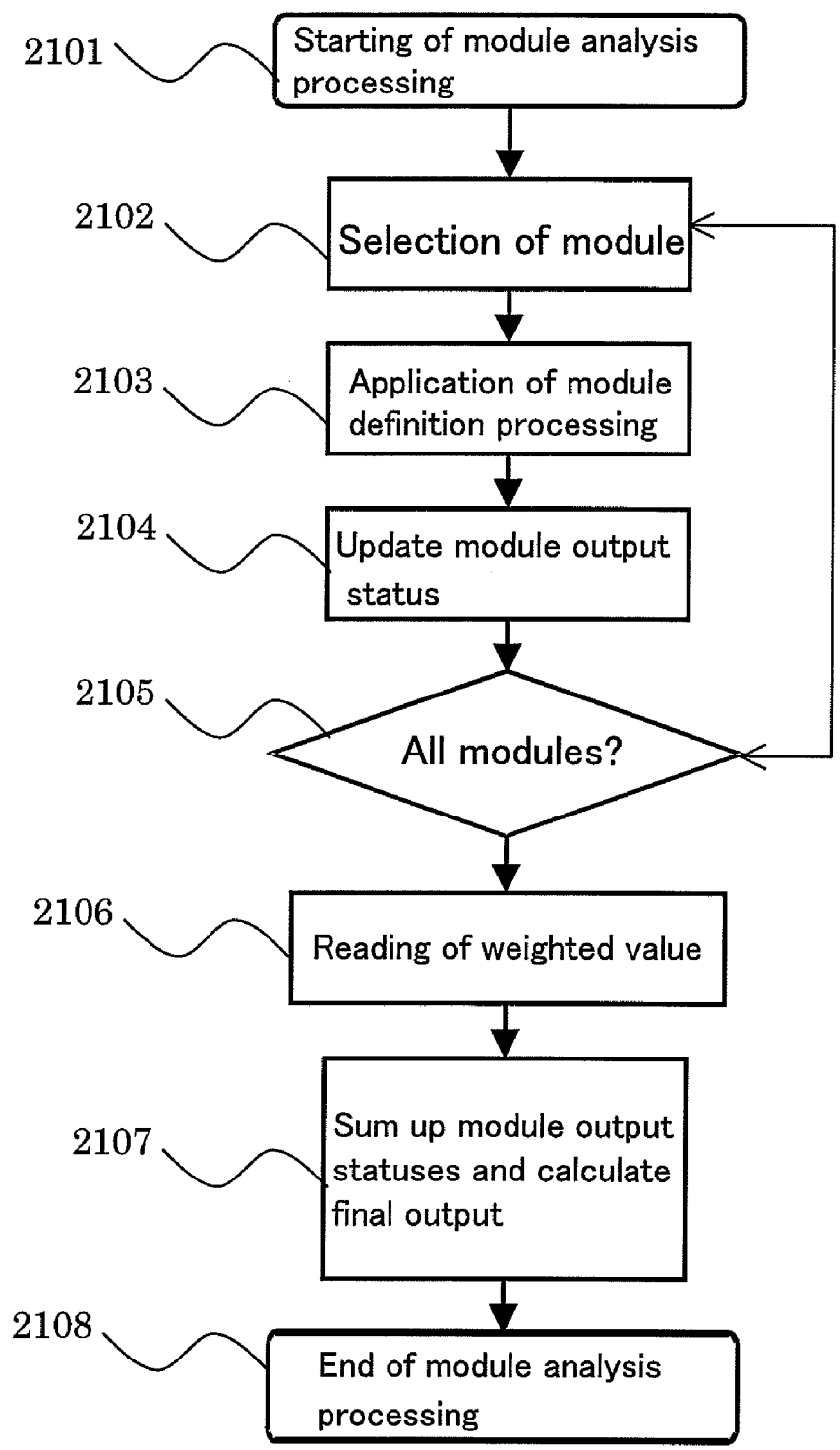
FIG. 21 is a flow chart to explain algorithm to calculate evaluation values, which indicate the condition of current brain activities by using the data shown in FIG. 20.

FIG. 21 is a flow chart of algorithm to calculate an evaluation value to express the current brain activity by using the data shown in FIG. 20. A thread program to be operated in background for each data sampling performed several times per second is called from 2101, and a series of analytical processing procedures are performed. Numeral 2102 represents an operation to call an agent module and its input unit according to the data recorded in 2001. In this case, if the called module is a primary agent, information of a matching sampler is used as the input. If the called module is a secondary or a tertiary agent, output information of another matching agent is used as its input. The contents of the outputs are calculated by calling the algorithm defined for each agent in the step 2002 with respect to these input values (Step 2103). The calculated content is stored in a buffer in Step 2104. The stored value is used as input information to another agent or is called for final output calculation or it is referred when it is called for final output calculation from the synthesizer unit. The procedures from 2102 to 2104 are repeatedly carried out to the registered module elements (Step 2105).

According to the routine 2004, the output value of each agent module is multiplied by the weighted value as read from the data 2005, and the total value is outputted (Steps 2106 and 2107). This result is written in the newest buffer area, and the thread processing is completed (Step 2108). In the processing of each evaluation as to be described later, the newest data written in this buffer area is used.

In the operation processing shown in FIG. 21, rewriting processing is performed on the results of investigation of the learning phase mode in the execution of the real-time operation phase mode to the data 2005 to be read in Step 2106. The procedure and the technique will be described in the operation procedure of the learning phase mode as given later.

By using real-time evaluation function prepared for each data sampling in the filtering processing as described above, description will be given now on the behaviors of the devices to be carried out in the learning phase mode. In the contents of the data stored in the information processing device 602, examples as many as C of the contents are included to explain and indicate introspective theme, which the user can carry out introspectively. By executing each of these contents as introspective activities, the function can be fulfilled as "instruction command". This contents module can be incorporated by the technique such as screen display, sound display, or touch display including Braille points. There are, for instance, the processing such as the singing in mind, the giving of image by moving fingers, the calculating by subtraction, or verse-capping.

Figure 11:
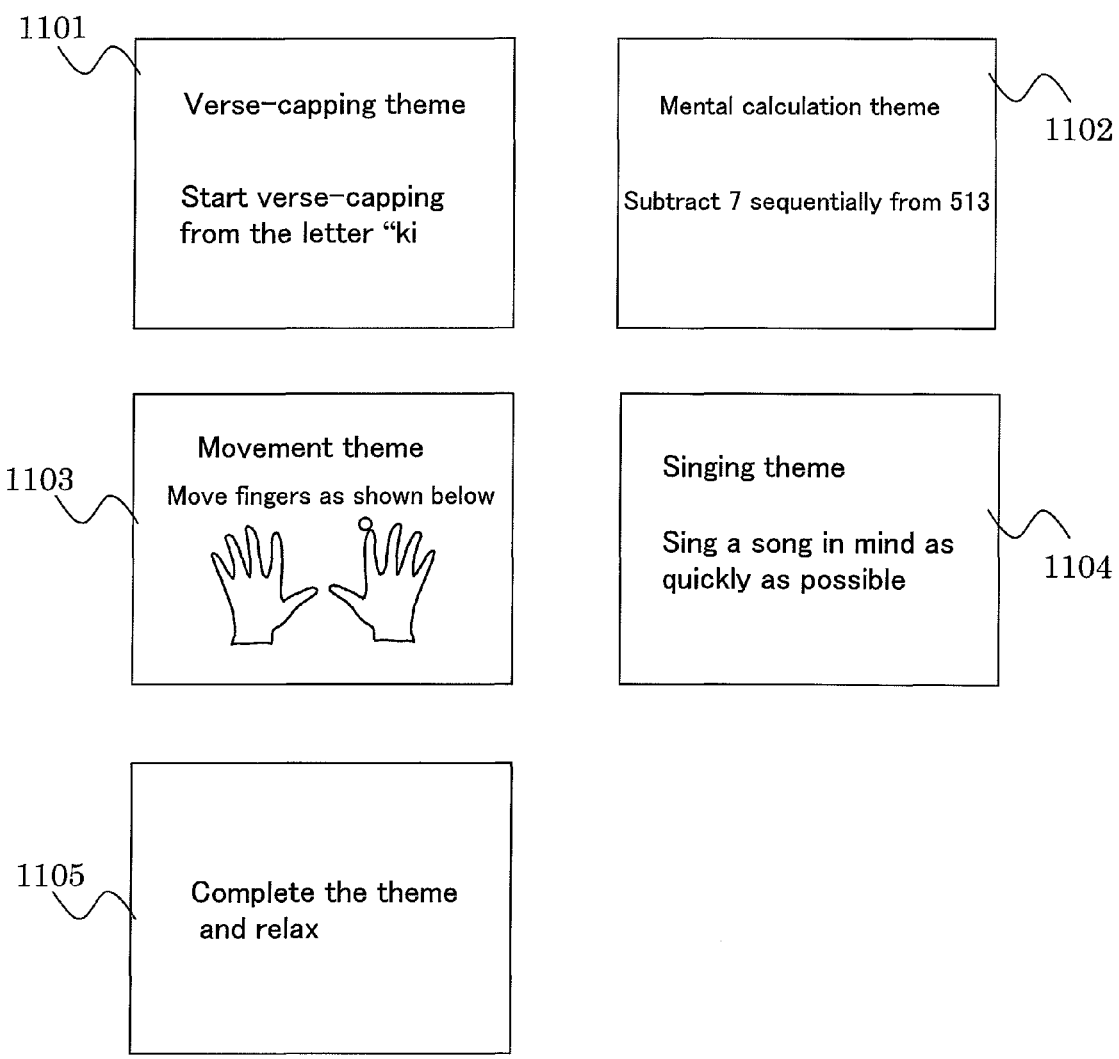
FIG. 11 represents drawings to explain examples of screen data of different themes.

FIG. 11 summarizes examples of screen to express the contents of these themes. These include example of display screens such as verse-capping theme 1101, mental calculation theme 1102, finger-moving image theme 1103, singing theme 1102. At the time of the completion of the theme, it is possible to ask the user to terminate the execution of the theme.

Figure 10:
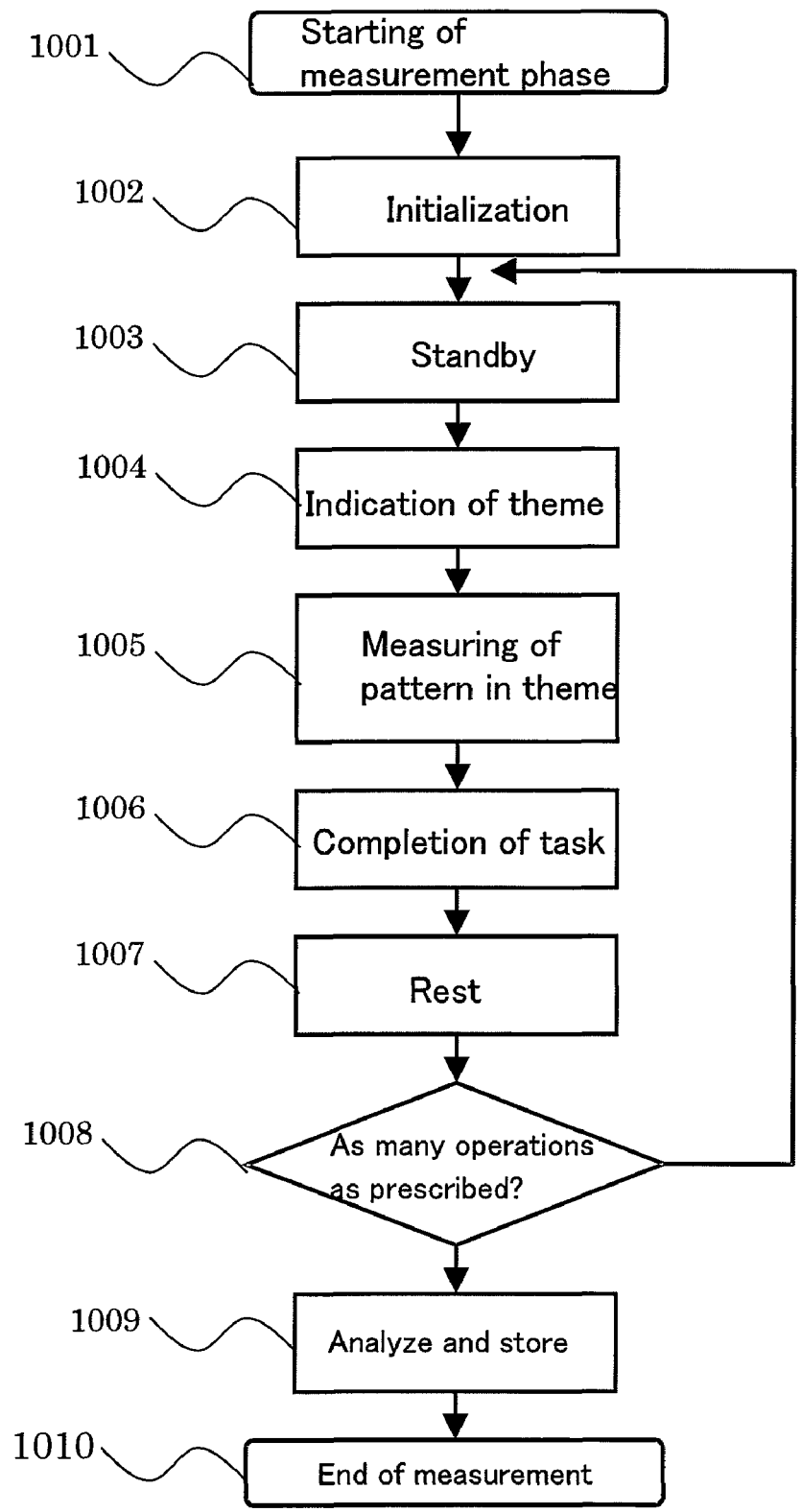
FIG. 10 is a flow chart to explain a subroutine to actually perform a calculation phase.

FIG. 10 is a flow chart to explain the processing of subroutine to carry out the calculation phase. First, description will be given below on various types of the initialization processing step 1002 of FIG. 10. When personal information medium is placed, the data is read, and the driving of the device is started. In the medium, the data when this device has been used by the user in the past are stored. The procedure to store and to use the data will be given later. A laser beam is projected from a light projector 103 as shown in FIG. 1. At the same time, the measurement is started at the receiver 105, and the measuring device 112 writes the information on record. At the same time, the information is transmitted to the information processing device 601. Thereafter, the measurement by NIRS sensor at each of the measuring positions is performed periodically until the measuring operation is turned off at Step 1010. From transmission light intensity of each wavelength, oxygenated hemoglobin concentration and reduced and total hemoglobin concentrations are calculated, and the transmission of the data to the information processing device 601 is continued. At the information processing device 601, the information is received by the technique of the thread programming known as general function of operating system (OS), and the information in the sampler 801 is continuously updated.

In the standby processing step 1003, a marker to be turned on and off for each predetermined time period is displayed on a monitor 603. This marker indicates the point to be gazed at (to be watched closely) and the timing of respiration (breathing). This procedure is repeatedly carried out for a certain period of time until the change of blood amount of the user 101 will be stabilized. In this case, the user remains in standby position in relaxed manner so that a specific intellectual activity may not be excessively performed.

Next, description will be given on the theme indicating step 1004. One of operation task screens 1101 to 1104 is displayed on the screen of the monitor 603. In the present embodiment, one of the four types of themes as described above is selected at random and is displayed on the screen, thereby asking the user to execute the theme.

Figure 12:
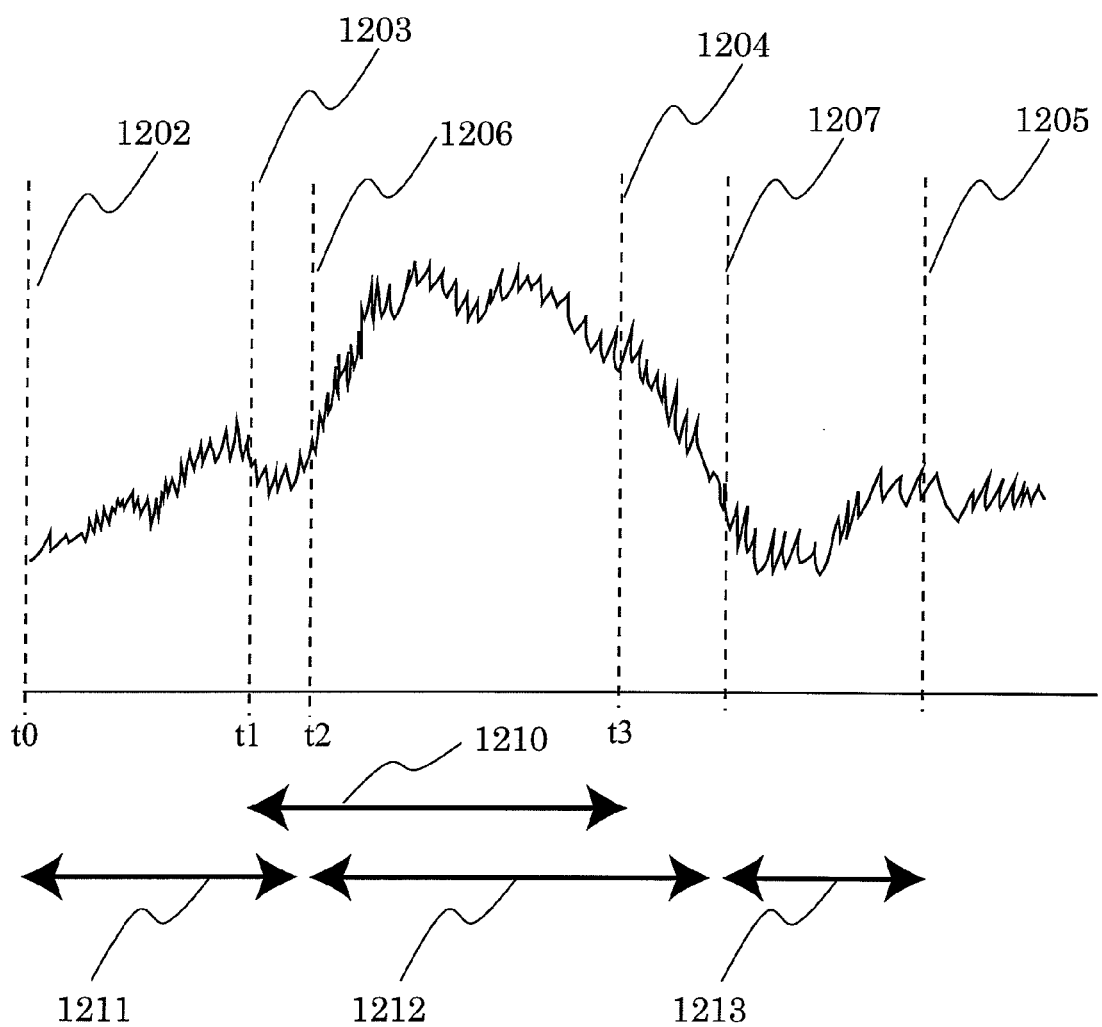
FIG. 12 is a diagram to explain examples of the data obtained from measurement of blood amount.

In the pattern measuring step 1005, the data of the change of cerebral blood amount during the activity of the user according to the instruction of the screen 603 are collected. FIG. 12 shows an example of the collected data. The data obtained during the execution of the task are transmitted and converted to agent function sequentially, and the data are stored as the information in time series.

When a predetermined time period has elapsed, the screen 1105 to indicate the termination of the theme is displayed (termination processing step 1006). Subsequently, it proceeds to a phase where the subject (user) is asked to take a rest (rest processing step 1007). Measurement is still continued during this period. After the execution of the theme has been completed, the data on the change of cerebral blood amount remains on the sampler as data. The operations of the agent and the synthesizer are continuously carried out, and the behaviors are temporarily stored on the main memory as log data. The above procedure is repeated as many times as prescribed.

In the above, an example has been described, in which each of the tasks is performed once each time by changing the sequence. It may also be so designed that a part of the listed tasks is executed or a specific task is executed once at a time or more. However, it is preferable that as many designated tasks as preset can be carried out without fail.

In Step 1009 of FIG. 10, evaluation is made as to whether or not the agent module is operating to match the activity of mental functions to the aimed theme. FIG. 12 is a block diagram to express the data in time series. Output value of the agent is taken on the axis of ordinate and the elapsed time is taken on the axis of abscissa in the graph. The information on the timing of the activity of mental functions to start or to terminate is received via a network 913 shown in FIG. 9.

Reference numeral 1203 in FIG. 12 represents the time when the theme is indicated and started (time t1) and the time to indicate the termination of the theme (time t2) with respect to the time axis on the axis of abscissa. Also, reference numeral 1202 represents time t0 before a certain fixed time from the time t1, and the reference numeral 1205 represents time t3, which is a time point after a certain fixed time period from the time t2.

It is supposed here that time delay required from the starting and/or the termination of the activity until the finding of the change of blood amount is defined as $\Delta 1$ and $\Delta 2$ respectively. However, each of the values of $\Delta 1$ and $\Delta 2$ is defined, for instance, as a value from 0 second to about 10 seconds, i.e. a value within an adequate range as determined from the finding of biological measurement in advance. Here, it is supposed that the time period, during which the change of blood amount is observed from "t+$\Delta 1$" (time 1206) to "t2+$\Delta 2$" (time 1207), is defined as a region A (1212), and that a time period, during which the change of blood amount goes back to (t0 ~t1+$\Delta 1$) 1211 and (t2+$\Delta 2$~t3) 1213, is defined as a region B.

In this case, as a reference value to determine the values of time delay $\Delta 1$ and $\Delta 2$, the value of each of $\Delta 1$ and $\Delta 2$ to satisfy a value (i.e. a value where an absolute value $|P1-P2|=P0$ of the difference when average value (P1 and P2) of time series is calculated will be at the highest) is searched from the range of the defined region and is determined.

As shown in FIG. 12, the value of the agent is changing even during the period of the region A. The average value of these changes and the standard deviation are calculated, and this value is defined as $\sigma 1$. The standard deviation of the changes in the region B is defined as $\sigma 2$. With respect to the data "i" of the repeating of a series of measuring operations, the value of $P0/(\sigma 1+\sigma 2)$ is defined as evaluation values E (g, t, s) of the measurement data. Here, the symbol "g" is the number of the agent, the symbol "t" represents a type of the task executed introspectively, and the symbol "s" is an index value to indicate the condition of the sensor in the setting. The calculation is performed for the final output values of the synthesizer respectively.

After calculation, the values of the data E and U are stored in the medium 605. FIG. 13 is a table to summarize data structure of an example of the stored information with the accumulated data. Sequential number is given for each setting, and the value is entered in the column 1301 of FIG. 13. Also, the time when the setting has been carried out is stored in the column 1302. A plurality of tasks are executed for each of these settings, and evaluation values such as type, time, and result of each task are stored in the column 1303. From these history data, variance in each task and variance in each setting are obtained.

The setting "s" changes each time when re-installation is made. The value "t" is a variable to indicate the type of the task. When the measurement of the data is repeated, the value E (I) is accumulated to be equal to the product of the number of measurements and the number of agents. After the measurement step 703 to each set of the theme has been terminated, processing of the evaluation value of the current condition is estimated to the current setting "s" (Step 704). For each of the agents, the result of the current measurement is compared with the result of the average value in the past, and the reliability of the reaction at the current setting is calculated. By using the information of history of the results to each task, an example of the technique to evaluate from the reaction in a specific setting will be described below.

Figure 7:
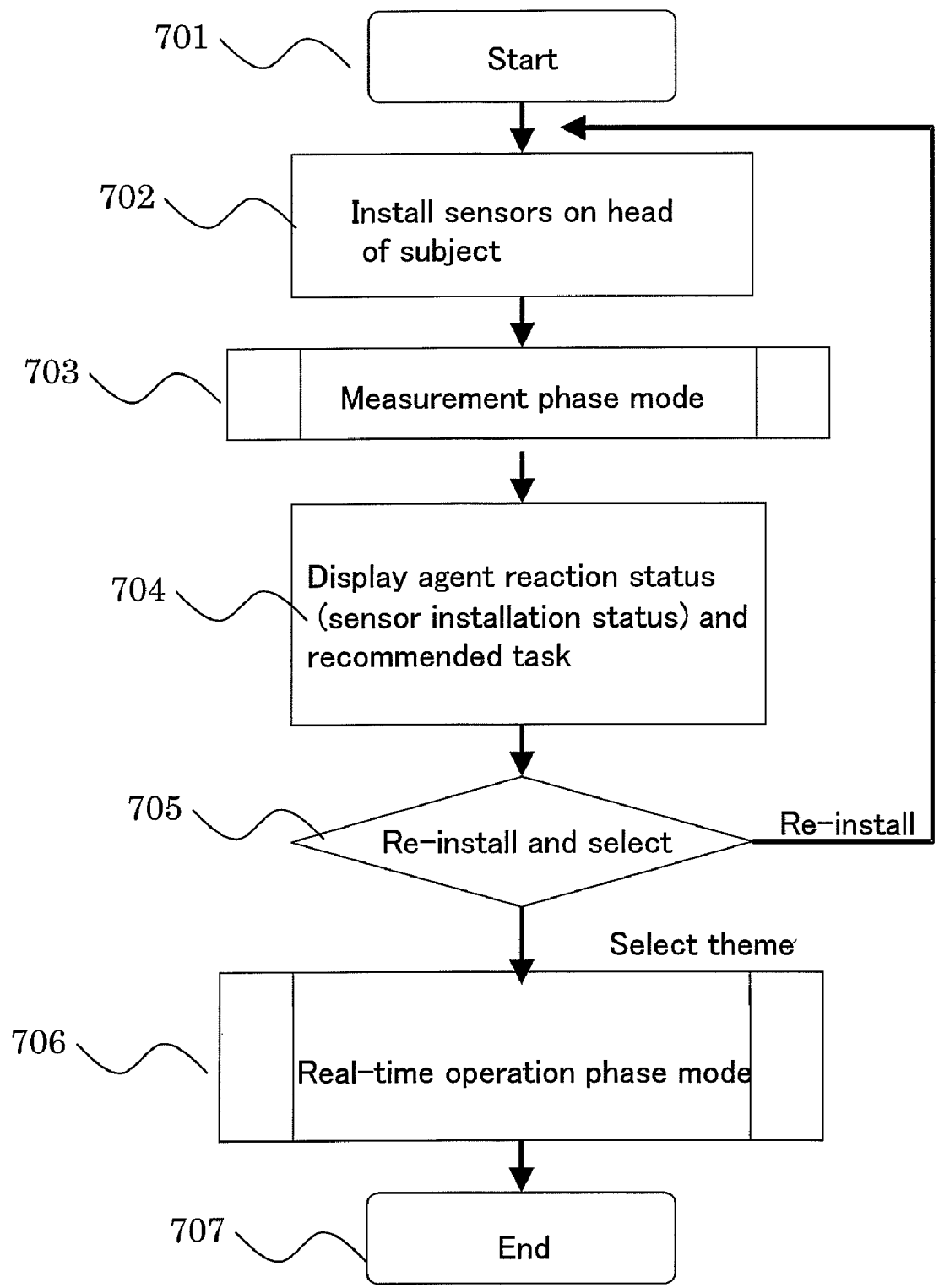
FIG. 7 is a flow chart to show operation procedure of Embodiment 1.

Through the step 703 shown in FIG. 7 and by the operation in the past, the past history of each of the agents is converted to parameters, and these data are stored in the medium. As described above, it is supposed that the symbol "g" represents the number of the agent, the symbol "t" represents the number of the task, and the symbol "s" stands for the state of the setting. The information stored in the database on the past history is expressed as E (g, t, s, k). This value is supposed to indicate the result of k-th measurement as obtained under a certain fixed condition [g, t, s].

Here, it is considered that the value E (g, t, s, k) is a value, which changes as a variable of t and g according to a certain probability distribution. For the measurement performed under a specific task "t" and a specific agent "g" to the value E (g, t, s, k), the average value in the entire history is set as E0 (g,t), and this value is stored in the medium 605. Also, the standard deviation is set as σ (g,t), and this is also stored in similar manner. This value σ (g,t) is multiplied by a constant, and the result of the multiplication is regarded as a value A (g,t) and this is used as a reference value for the reaction to the theme tasks of subsequent agents.

Based on the history, the sharpness of the agent to react to the tasks is evaluated in the following procedure: The average value E0 (g,t) is divided by A (g,t), and this result is defined as a value B (g,t). If this value is higher than 1, it is judged that the agent "g" is an agent to indicate significantly positive reaction to the task "t", and a positive weighted value "W (g,t)=B (g,t)-1.0" is given to it. If the value B (g,t) is lower than −1, negative weighting "W (g,t)=B (g,t)+1.0" is carried out. In other cases, it is regarded as unstable state where both positive reaction and negative reaction are observed, and it is defined as: W (g,t)=0.0. These types of information are also stored in the medium 605.

Description will be given below on a method to evaluate the condition of the setting "s" by using the information stored in the medium 605 when a data E1 (g, t, s, k) is obtained from the execution of a certain theme "t" under a certain setting "s". It is considered that the value E1 (g, t, s, k) is a sample of probability distribution based on normal distribution of the average value E0 (t,g) and the standard distribution (t,g), and verification procedure is performed according to null hypotheses.

If the result of this verification was significantly different, it is judged that the change at the current setting "g" is significantly different compared with normal setting conditions. In such case, the theme is repeatedly executed under the same condition "t" again, and re-verification is performed by increasing the number of k. If this result is still significantly different, display is given on the screen 603 to show that the behavior of the agent to the task "g" is improper. Thus, the position of the sensor, to which the sampler used as an input of the agent "g" is related, is displayed on the screen.

In case the result of the above verification is not significant, it is judged that the change at the current setting "s" is within the tolerance range as the behavior of the agent. Then, average value of E1 (g, t, s, k) for the value k is regarded as the value E2 (g,t). Then, similarly to the preceding step, a value by subtracting 1 from the absolute value of "E2 (g,t)−A (t,g)" is used as W1 (t,g) in the current setting conditions.

After the above verification for each agent "g" and the task "t" has been completed, average value and variance of the data of W1 (t,g) are obtained with respect to the value "t". If the average value of the value W1 (t,g) and the value of the history up to the present moment are significantly higher, it is quite possible that the conditions of the agents have not been accurately collected.

In this respect, the display that the behavior of the agent "g" is improper is given again, and the position of the sensor, to which the sampler used as an input of the agent "g" is related, is displayed on the screen, and the subsequent operation is performed without using this agent. Or, it is urged to select whether the setting is to be carried out again or the measurement phase is to be executed again. Average value and variance are taken on the data of W1 (t,g) with respect to "g". In case the average of the values and the difference between the average of the values and the value of the history is significantly higher, it is quite possible that the condition of execution of the task was unstable. For this reason, the task with poor result is displayed, and it is re-confirmed to the user 101 whether there has been any problem or not in the condition when the task was executed. The user 101 re-confirms the condition of the execution of the task, and measurement is made again. Or, it is avoided to use the task as the command in the setting at this moment, or the value of the data 2005 as read on the main memory is changed so that the weighting of the corresponding agent is decreased at a certain predetermined ratio.

The use of these techniques brings several advantages. The first advantage is that extreme demand can be avoided on the contact of the sensor. Even when perfect contact is not found at a point of the sensor, operation can be carried out in the real-time operation phase even when no action is taken if an important agent is not referred. The second advantage is that the information on the past history can be used for the value A (g,t), for which many trials are needed to ensure stable result of estimation. The third advantage is that the reference standard can be calculated, by which it is possible to differentiate whether it is a problem caused by repetitive execution or it is a problem caused by the reaction of the agent.

Figure 14:
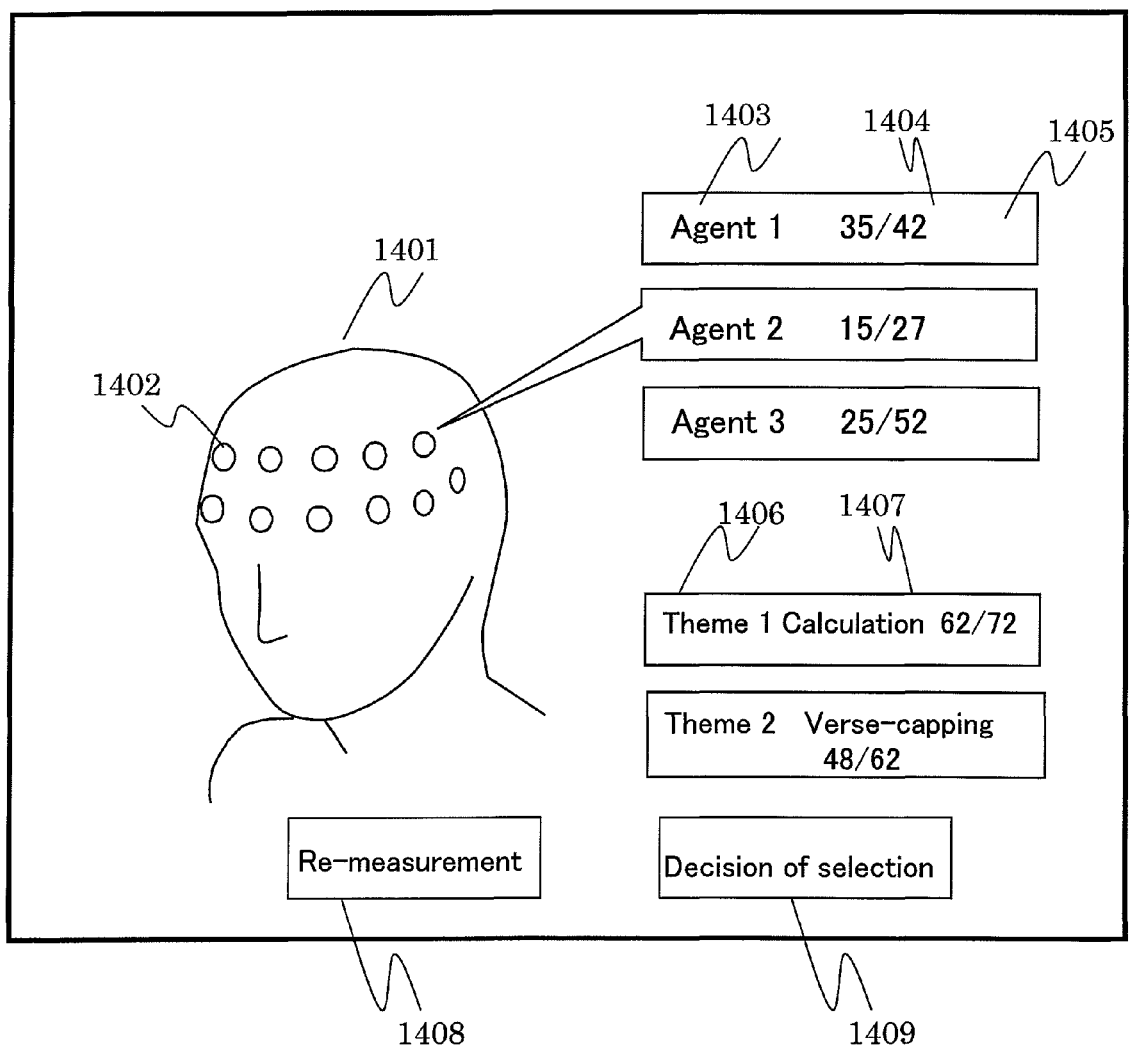
FIG. 14 is a drawing to explain an example of a screen to represent a starting condition of an agent and to promote selection of the condition.

From the result of the step 703 (measurement phase mode), calculation is made on the condition of reaction of the agent, and a sensor point is displayed, which is estimated to have caused the problem in the acquisition of the aimed information, or a combination of the themes is displayed, which can be acquired efficiently under the current reaction state. FIG. 14 shows an example of such display screen. A screen of the monitor 603 is shown in FIG. 14. On left side of the screen, markers 1402 each indicating a measuring point is disposed on a standard human model 1401 prepared as a three-dimensional model. On the right side of the screen, an agent 1403 related to physical information and a list of information 1406 correlated with introspective theme are displayed, and reliability accuracies 1404 and 1407 in the current measurement and standard reliability accuracies 1405 and 1408 calculated from the history are displayed.

As the value of this reliability accuracy, the value obtained by calculation can be directly applied, or entertainment features can be promoted by converting to the full marks. When the user selects one of the listed elements, the selection is reflected in the color of the marker 1402, which corresponds to the measuring point correlated to the analysis of the agent. When the list element correlated to the introspective theme is selected, it is reflected in the amount of weighting and the intensity of color correspondingly. In this case, the reliability accuracy of the sensor calculated in the preceding step 703 is displayed as the number of flashings per second of the marker.

The user confirms the result of reliability accuracy related to this task. When the sensor is re-installed and measurement is repeated, a console button 1408 for re-calculation is selected, and the procedure is repeated from the step 702. If the theme is found, which may satisfy the reliability accuracy to be operated adequately as the command, a console button 1409 for selection decision is selected, and it proceeds to the next real-time operation phase mode 706 (Step 705).

In the real-time operation phase mode (step 706), the user performs introspective activity to change cerebral blood amount to match the subject's intention, and the display is changed by reflecting the result. When the user performs the activity while observing the reflected result, an effect is provided to promote the feedback with consciousness to execute adequate operation. Description will be given below on the behavior of the device in the real-time operation phase mode by referring to the block diagram shown in FIG. 15.

In the initialization processing step 1502, the initialization of the variable needed in the reflection updating processing step as to be described later is performed. Also, the learning data in the past stored in the step 703 and the step 704 are read. In a screen display step 1503, a selection screen similar to the one displayed in the previous step 704 is displayed. In a technique selection processing step 1504, the reliability accuracies of introspective theme calculated in the previous step 704 and displayed in the step 705 are displayed on the screen of the monitor 603. The user selects either one of them. As the command to deliver an instruction in the reflection updating step 1505 as to be described later, operation can be carried out by executing the introspective theme.

Figure 16:
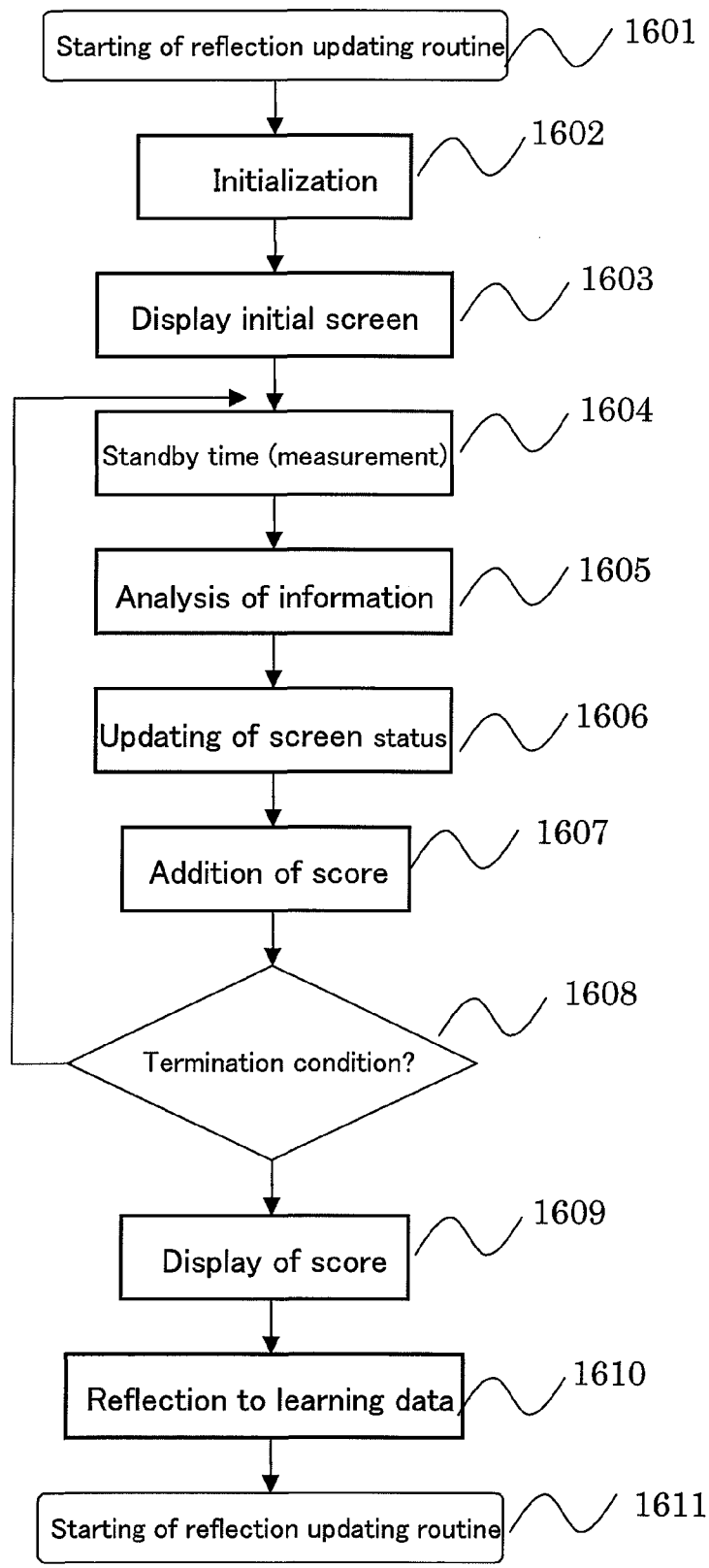
FIG. 16 is a flow chart to explain a subroutine for carrying out a reflection updating phase.
Figure 17:
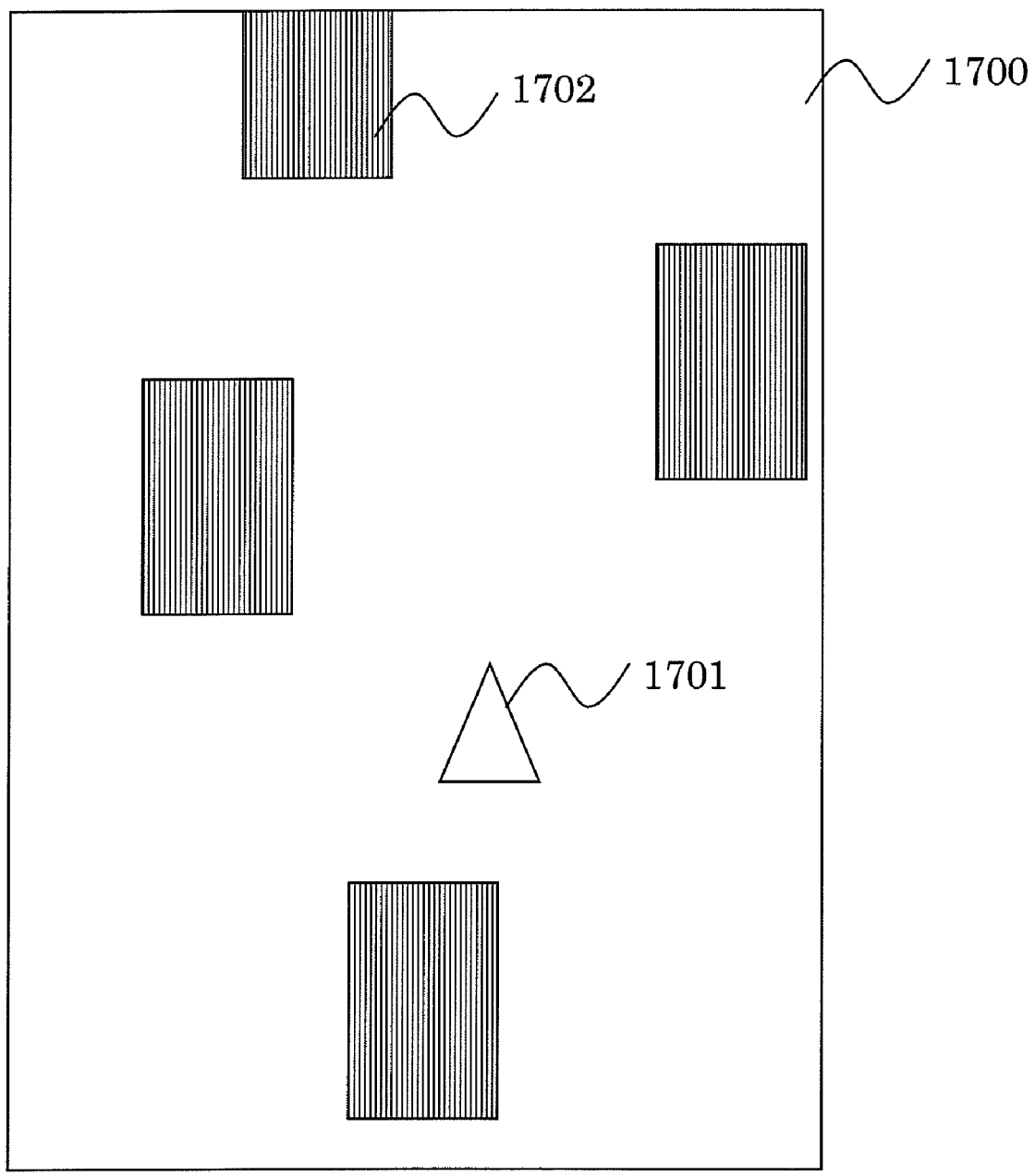
FIG. 17 is a drawing to explain an example of screen to be displayed in the reflection updating phase as an object of operation.

The operation of the reflection updating processing step 1505 is carried out by a subroutine module. Referring to the flow chart of FIG. 16, description will be given now on an example of the packaging of this module. FIG. 17 shows an example of an image of the screen executed by this module. On a screen 1700, a cursor 1701 operated by the user and a target position 1702 are displayed. The target position 1702 is displayed on background screen, and the background screen is scrolled in downward direction at a constant speed at each updating.

The initialization processing is performed in the step 1602. The position of the cursor 1701 is displayed at the center of the screen.

In step 1603, initialization screen is displayed on the monitor 603.

In the step 1604, for the purpose of maintaining the moving speed, standby processing is performed for a short time. This standby processing is carried out for a time period of several tens of milliseconds to several hundreds of milliseconds. Even during the standby of the screen updating processing, the measurement of cerebral blood amount data is continued.

In the step 1605, the measurement data of the blood amount at the most up-to-date moment is applied on signal processing of the device 601 as described above, and the output result is calculated. When operation of a delayed agent is used, information on the blood amount in the past as stored in the sample 801 is also used for the judgment.

In the Step 1606, the information is updated. To match the output value as given above, the cursor is moved to the left or the right. The background picture is moved downward, and the screen is updated to match the updated information.

In the Step 1607, the current state or condition is evaluated. If the position of the cursor is within the area of the target position 1702, the score is added.

As the condition to terminate the operation, it is confirmed that a specific score and the time as prescribed satisfy a predetermined reference. If the condition of termination is not satisfied, the procedures in Steps 1604-1607 are repeated. If the condition of termination are satisfied, it proceeds to the Step 1610.

In the Step 1610, the termination of the real-time searching phase is notified on the screen of the monitor 603. The scores are calculated, and the result is displayed. In order to reflect this result to the learned data in the Step 1508, the result is temporarily stored in the area of the variable (Step 1610).

Figure 15:
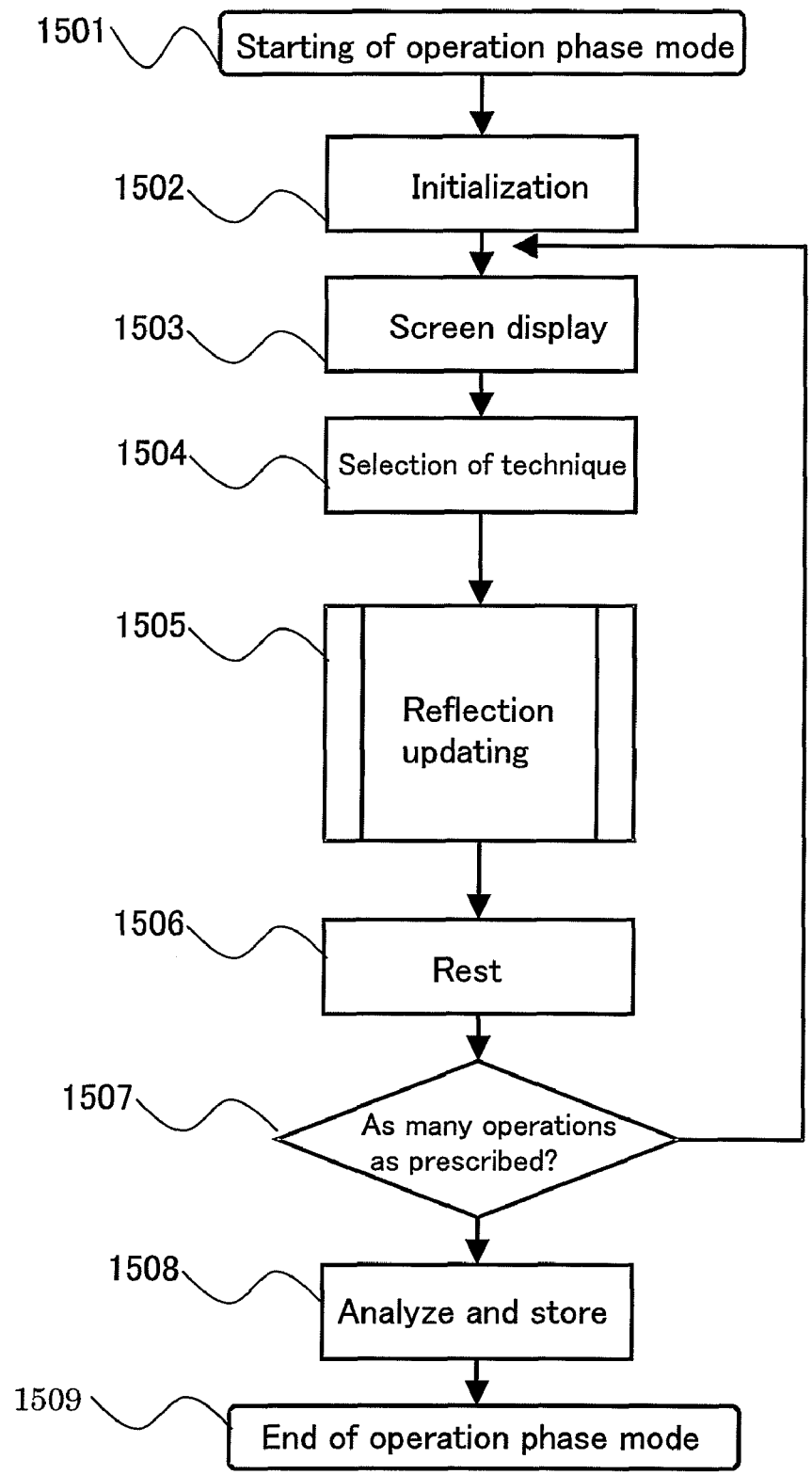
FIG. 15 is a flow chart to explain a subroutine for carrying out operation phase.

Now, the subroutine 1505 shown in FIG. 15 has been completed. Subsequently, the procedure enters a phase to make the subject to take a rest (rest processing step 1506). However, measurement is continued during this period, and the data of the change of cerebral blood amount, which returns to normal status after completing the execution of the theme, is electronically stored in the log.

The procedures in the Steps 1503-1506 are repeated as many times as required (e.g. 5 times). When the predetermined number of repeating operations has been reached, the searching phase mode is terminated. Average score in the current operation phase 706 is stored in the medium 605.

Average value and variance of the scores in the measurement performed so far are compared in the medium, and the result (standard deviation) is multiplied by a constant term, and this is added to a value S(i), which indicates the condition of installation of each agent actually used as a compensation value of the current measurement. Now, the operation phase mode has been completed (Step 1509).

According to the Embodiment 1, localized brain functions can be measured by optical brain function measuring device, and selection and training on the theme for instruction command can be adjusted to match the depth or the degree of the learning of the user and the instability of the sensor when measurement signal is used as an input signal to the external device, and these can be used in combination to be suitable for the conditions of setting, which vary from day to day.

Embodiment 2

Figure 18:
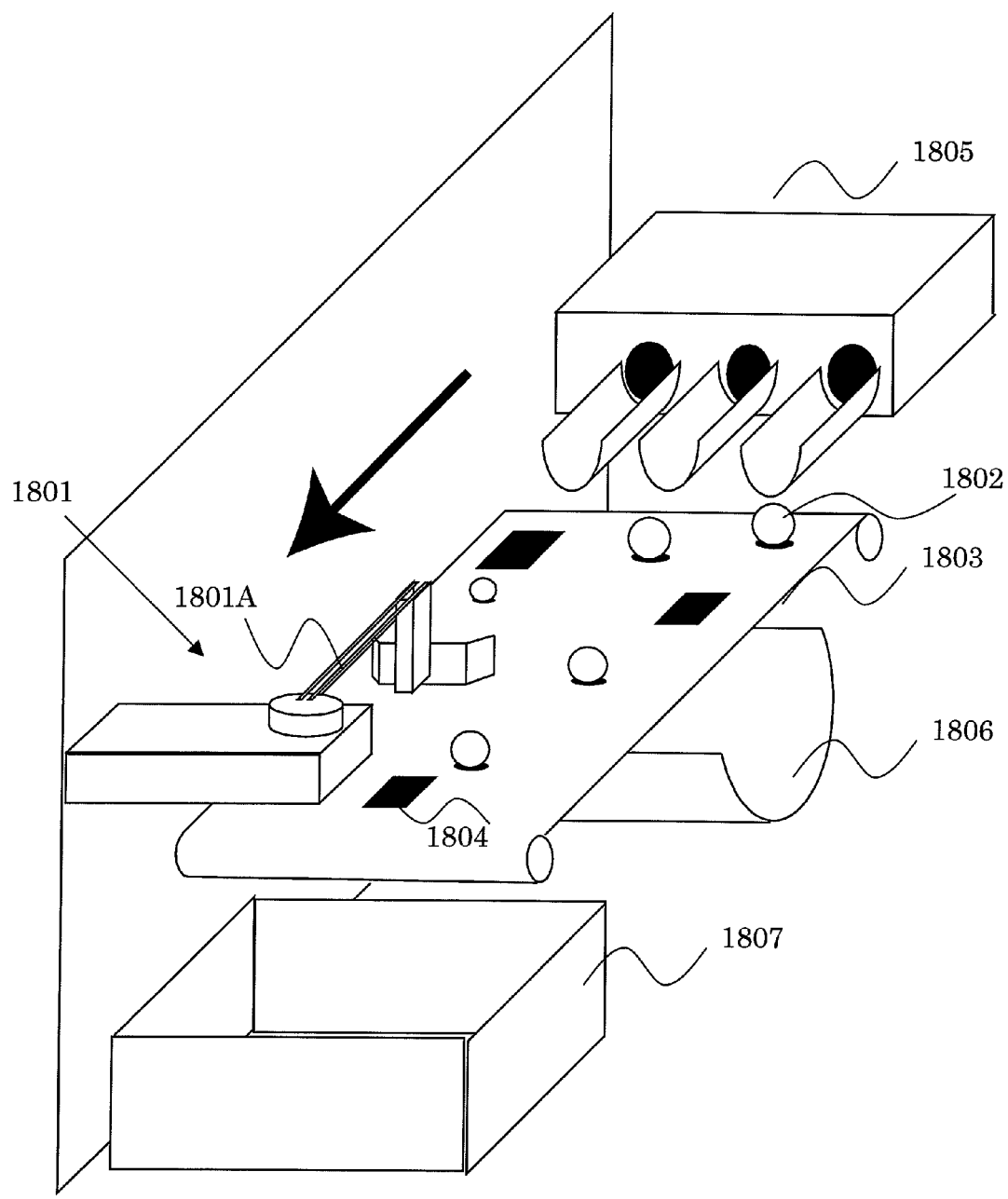
FIG. 18 is a schematical perspective view to explain an example of a device to be used in the reflection updating phase as an object of operation.

In the Embodiment 2, subroutine module in the real-time operation phase mode in computer is executed by actual devices. FIG. 18 is a perspective view to explain an example of the device actually operated. In the Embodiment 2, instead of the position of the cursor used in the Embodiment 1, position and angle of an arm 1801A are controlled in a selection device 1801 designed in form of a shovel. In the Embodiment 1, the background moves. In the Embodiment 2, a belt conveyor 1803 carrying an object 1602 on it moves in the direction of thick arrow. The objects 1802 are periodically discharged to the belt conveyor 1803 from an object discharger 1805. Holes 1804 are disposed on the belt conveyor 1803. By moving an arm 1801A into the hole 1804 at adequate timing, the object can be dropped to a first collector 1806 from the belt conveyor 1803. The object, which was not dropped to the first collector 1806 by the selection device 1801, is dropped to a second collector 1807.

Figure 19:
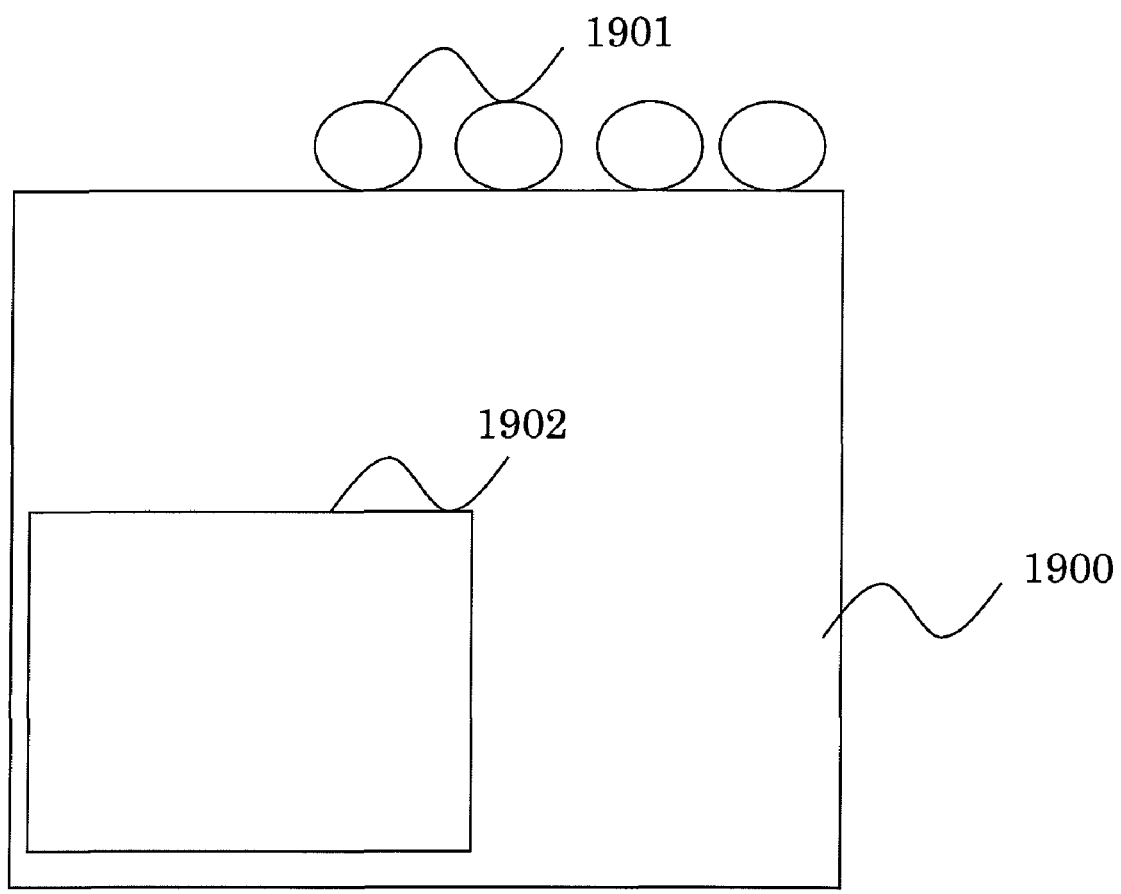
FIG. 19 is a drawing to explain an example of a device to be used in the reflection updating phase as an object of operation.

FIG. 19 is a block diagram of a general-purpose processing device, which can be used as a packaged device. The packaged device 1900 is another example of the general-purpose information processing device, which is actually operated according to the present invention. On this general-purpose information processing device, there are provided a number of lights 1901 and a sound source 1902. In the Step 1505, an amount to match the introspective theme is calculated by applying the current blood amount information to the processing device 602. To match the calculated value, light amount of the light source, and sound volume and sound pitch of the sound from the sound source are adjusted. By following the changes at all times, the device can fulfill the function as a simple device, which is driven by voluntary operation of the user.

According to the Embodiment 2, localized brain functions can be measured by optical brain function measuring device, and selection and training on the theme for instruction command can be adjusted to match the depth or the degree of the learning of the user and the instability of the sensor when measurement signal is used as an input signal to the external device, and these can be used in combination suitable for the conditions of setting, which vary from day to day.

INDUSTRIAL APPLICABILITY

The present invention can be applied—not only in the transport and carrying devices such as information processing devices, video game devices, electric household appliances, audio-visual devices, transport devices, etc. but also in various types of instruments and devices to be controlled by behavior and thinking of a human subject.

The invention claimed is:

1. An external condition control device based on measurement of brain functions to control an external device to match changes in blood amount at a number of sites on a brain of a subject acquired by near infrared spectroscopy by using a multi-channel fiber holder installed on outer side of a head of the subject the external condition control device comprising:
   a plurality of samplers receiving measurement data of the blood amount measured at the sites of the brain;
   a plurality of primary agents receiving information of the blood amount at the sites of the brain from the plurality of samplers, converting the information of the blood amount to primary output values;
   a plurality of secondary agents receiving the primary output values, converting the primary output values to secondary output values;
   a plurality of tertiary agents converting the primary output values and the secondary output values to tertiary output values by using learning parameters obtained from a synthesizer;
   the synthesizer integrating the secondary output values and the tertiary output values based on a weighted linear sum of the secondary output values and the tertiary output values and outputting a result of integration to control the external device;
   a medium storing weights used for the weighted linear sum at the synthesizer and statistical data of output value history of each of the plurality of primary, secondary, and tertiary agents;
   a measurement phase mode operation means for providing an introspective theme to be executed by the brain and measuring the blood amount by using a current setting of the fiber holder while the brain executes the introspective theme; and
   an evaluation means for comparing the statistical data of the output value history and an output value in the measurement phase mode for each of the plurality of primary, secondary, and tertiary agents, and calculating a reliability value for each of the plurality of primary, secondary, and tertiary agents in the current setting of the fiber holder,
   said evaluation means compares the output values of the measurement phase mode with the past statistic values for every agent of the plurality of primary, secondary, and tertiary agents, and calculates the reliability values for every agent of the plurality of primary, secondary, and tertiary agents,
   wherein the weights used for the weighted linear sum at the synthesizer are determined based on the reliability value for each of the plurality of primary, secondary, and tertiary agents in the current setting of the fiber holder.

2. An external condition control device based on measurement of brain functions according to claim 1,
   wherein the external condition control device further comprises:
   a monitor for monitoring installation condition of the fiber holder and an evaluation result of the evaluation means, and for displaying data on a screen to promote re-installation of the fiber holder and/or changes of the weights.

* * * * *